(12) United States Patent
Whitcher et al.

(10) Patent No.: US 9,321,001 B2
(45) Date of Patent: Apr. 26, 2016

(54) PORTABLE OXYGEN CONCENTRATOR WITH INTEGRATED MANIFOLD

(75) Inventors: Douglas Adam Whitcher, Atlanta, GA (US); Bradley Stewart Koeppel, Smyrna, GA (US); Jeremy Webster Blair, Atlanta, GA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/343,392

(22) PCT Filed: Sep. 7, 2012

(86) PCT No.: PCT/IB2012/054639
§ 371 (c)(1),
(2), (4) Date: Mar. 7, 2014

(87) PCT Pub. No.: WO2013/038315
PCT Pub. Date: Mar. 21, 2013

(65) Prior Publication Data
US 2014/0224126 A1 Aug. 14, 2014

Related U.S. Application Data

(60) Provisional application No. 61/533,962, filed on Sep. 13, 2011.

(51) Int. Cl.
*B01D 53/02* (2006.01)
*B01D 53/04* (2006.01)
(Continued)

(52) U.S. Cl.
CPC ....... *B01D 53/0407* (2013.01); *A61M 16/0677* (2014.02); *A61M 16/101* (2014.02);
(Continued)

(58) Field of Classification Search
CPC .......... A61M 16/0677; A61M 16/101; A61M 2016/1025; A61M 2205/8212; B01D 2253/108; B01D 2256/12; B01D 2257/102; B01D 2259/40009; B01D 2259/4533; B01D 2259/4541; B01D 53/0407; B01D 53/0415; B01D 53/0446; B01D 53/0454; C01B 13/0259; Y10T 29/49826
See application file for complete search history.

(56) References Cited

U.S. PATENT DOCUMENTS 4,859,217 A  8/1989  Chao
5,531,807 A  7/1996  McCombs
(Continued)

FOREIGN PATENT DOCUMENTS

| WO | WO2013038299 A1 | 3/2012 |
|---|---|---|
| WO | WO2013038297 A1 | 3/2013 |
| WO | WO2013038315 A1 | 3/2013 |
| WO | WO2013038319 A1 | 3/2013 |

*Primary Examiner* — Christopher P Jones
(74) *Attorney, Agent, or Firm* — Michael W. Haas

(57) ABSTRACT

Methods and system for concentrating oxygen include a plurality of sieve beds configured to absorb nitrogen from air, at least one reservoir configured to store oxygen-enriched gas exiting from the plurality of sieve beds, a compressor configured to deliver air at one or more desired pressures to the plurality of sieve beds, a support member positioned in housing and configured to support the compressor, the plurality of sieve beds and the reservoir, an air manifold providing a plurality of channels therein that at least partially define passages communicating between the compressor and the plurality of sieve beds, and an oxygen delivery manifold providing a plurality of channels therein that at least partially define passages for delivering the oxygen-enriched to a user. The air manifold and the oxygen delivery manifold are integrally formed with the support member.

16 Claims, 16 Drawing Sheets

(51) Int. Cl.
*C01B 13/02* (2006.01)
*A61M 16/06* (2006.01)
*A61M 16/10* (2006.01)

(52) U.S. Cl.
CPC ........ B01D53/0415 (2013.01); B01D 53/0446 (2013.01); C01B 13/0259 (2013.01); *A61M 2016/1025* (2013.01); *A61M 2205/8212* (2013.01); *B01D 53/0454* (2013.01); *B01D 2253/108* (2013.01); *B01D 2256/12* (2013.01); *B01D 2257/102* (2013.01); *B01D 2259/40009* (2013.01); *B01D 2259/4533* (2013.01); *B01D 2259/4541* (2013.01); *Y10T 29/49826* (2015.01)

(56) References Cited

U.S. PATENT DOCUMENTS

| | | |
|---|---|---|
| 6,520,176 B1 | 2/2003 | Dubois |
| 6,764,534 B2 | 7/2004 | McCombs |
| 7,135,059 B2 | 11/2006 | Deane |
| 7,368,005 B2 | 5/2008 | Bliss |
| 7,402,193 B2 | 7/2008 | Bliss |
| 7,524,365 B2 | 4/2009 | Lin |
| 7,794,522 B2 | 9/2010 | Bliss |
| 7,837,761 B2 | 11/2010 | Bliss |
| 2005/0045040 A1 | 3/2005 | McCombs |
| 2005/0103341 A1 | 5/2005 | Deane |
| 2006/0117957 A1 | 6/2006 | McCombs |
| 2006/0230929 A1 | 10/2006 | Bliss |
| 2008/0257145 A1 | 10/2008 | Sprinkle |

PORTABLE OXYGEN CONCENTRATOR WITH INTEGRATED MANIFOLD

CROSS-REFERENCE TO RELATED APPLICATIONS

This patent application claims the priority benefit under 35 U.S.C. §371 of international patent application No. PCT/IB2012/054639, filed Sep. 7, 2012, which claims the priority benefit under 35 U.S.C. 119(e) of U.S. Provisional Application No. 61/533,962 filed on Sep. 13, 2011, the contents of which are herein incorporated by reference.

BACKGROUND OF THE INVENTION

1. Field of the Invention

The present disclosure pertains to a system and method for providing oxygen, and, in particular, a portable apparatus for concentrating oxygen by adsorption from air and methods for using such apparatus.

2. Description of the Related Art

Lung diseased patients often need supplemental oxygen to improve their comfort and/or quality of life. Stationary sources of oxygen are available, e.g., oxygen lines in hospitals or other facilities, that may provide oxygen to patients. To allow some mobility, cylinders of pure and/or concentrated oxygen can be provided that a patient may carry or otherwise take with them, e.g., on pull-along carts. Such cylinders, however, have limited volume and are large and heavy, limiting the patient's mobility.

Portable devices have been suggested that concentrate oxygen from ambient air to provide supplemental oxygen. For example, U.S. Pat. Nos. 5,531,807 6,520,176, 6,764,534, 7,368,005, 7,402,193, 7,794522, and 7,837,761 disclose portable oxygen concentrators that separate nitrogen from ambient air, and deliver a stream of concentrated oxygen that may be stored in a tank or delivered directly to patients.

SUMMARY OF THE INVENTION

It is an object of one or more embodiments to provide a portable oxygen concentrator that includes a housing; a plurality of sieve beds configured to absorb nitrogen from air, each sieve bed comprising a first end port and a second end port; at least one reservoir configured to store oxygen-enriched gas exiting from the second end ports of the plurality of sieve beds; a compressor configured to deliver air at one or more desired pressures to the first end ports of the plurality of sieve beds; a support member positioned in the housing and configured to support the compressor, the plurality of sieve beds and the reservoir; an air manifold providing a plurality of channels therein that at least partially define inlet air passages communicating between the compressor and the first end ports of the plurality of sieve beds; and an oxygen delivery manifold providing a plurality of channels therein that at least partially define inlet air passages for delivering the oxygen-enriched to a user. The air manifold and the oxygen delivery manifold are integrally formed with the support member.

It is yet another aspect of one or more embodiments to provide a method of manufacturing a portable oxygen concentrator is provided. The portable oxygen concentrator includes a housing; a plurality of sieve beds, each sieve bed in the plurality of sieve beds including a first end port and a second end port, a reservoir storing oxygen-enriched gas exiting from the second ends of the plurality of sieve beds, and a compressor. The method includes forming a support member configured to support the compressor, the plurality of sieve beds and the reservoir, integrally forming an air manifold with the support member and integrally forming an oxygen delivery manifold with the support member. The support member is configured to be positioned in the housing. The air manifold includes a plurality of channels therein that at least partially define inlet air passages communicating between the compressor and the first end ports of the plurality of sieve beds. The oxygen delivery manifold includes a plurality of channels therein that at least partially define inlet air passages for delivering the oxygen-enriched to a user.

It is yet another aspect of one or more embodiments to provide a system configured to concentrate oxygen that includes compressing means for generating a supply of compressed air from a supply of air; separating means for providing a supply of oxygen-enriched gas from the supply of compressed air; oxygen storing means for storing the oxygen-enriched gas; supporting means for supporting the compressing means, the separating means and the oxygen storing means; air delivery means for communicating air between the compressing means and the separating means; and oxygen delivery means for delivering the oxygen-enriched to a user. The air delivery means and the oxygen delivery means are integrally formed with the supporting means.

These and other objects, features, and characteristics of the present embodiments, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of any limits.

DETAILED DESCRIPTION OF EXEMPLARY EMBODIMENTS

Figure 1:
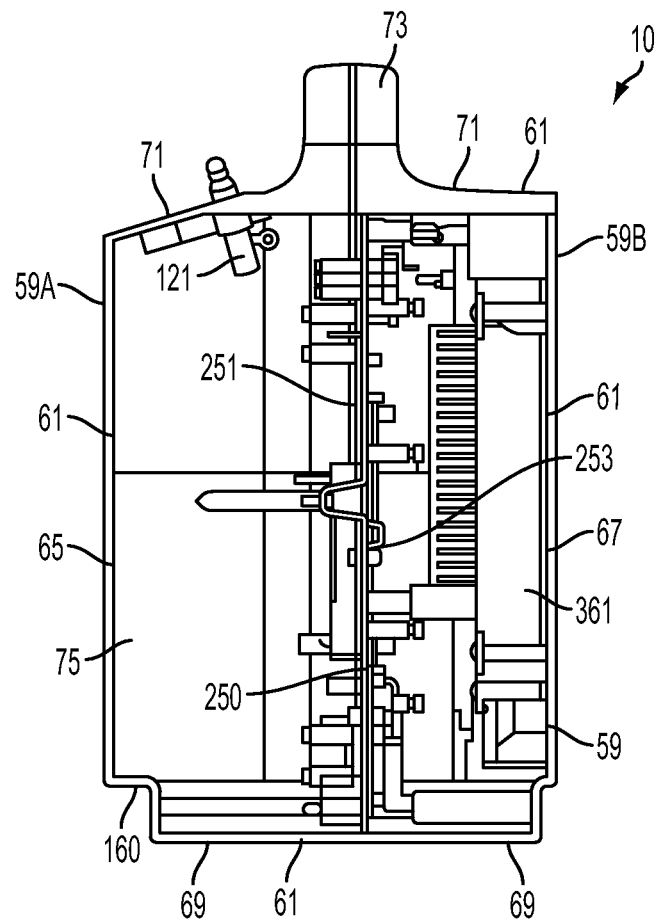
FIG. 1 is a side cross-sectional view of a portable oxygen concentrator (for sake of clarity compressor, air inlet filter, sieve beds, reservoir and controller are not shown) in accordance with an embodiment of the present disclosure.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIGS. 1-4B show an exemplary embodiment of a portable oxygen concentrator 10. Portable oxygen concentrator 10 includes a housing 59, a plurality of sieve beds 12 configured to absorb nitrogen from air, a reservoir 18 configured to store oxygen-enriched gas exiting from sieve beds 12, a compressor 14 configured to deliver air at one or more desired pressures to first end ports 32 of sieve beds 12, a support member 250, which may form a central chassis or spine, positioned in housing 59 and configured to support compressor 14, sieve beds 12 and reservoir 18, an air manifold 16 providing a plurality of channels 67 therein that at least partially define inlet air passages 64-68 communicating between compressor 14 and first end ports 32 of sieve beds 12, and an oxygen delivery manifold 102 providing a plurality of channels 67 therein that at least partially define passages 108 for delivering the oxygen-enriched gas to a user. Air manifold 16 and oxygen delivery manifold 102 are integrally formed with support member 250.

Optionally, portable oxygen concentrator 10 may include one or more additional components, e.g., one or more check valves, filters, sensors, electrical power sources (not shown), and/or other components, at least some of which may be coupled to a controller 22 (and/or one or more additional controllers, also not shown), as described further below. It will be appreciated that the terms "airflow," "air," or "gas" may be used generically herein, even though the particular fluid involved may be ambient air, pressurized nitrogen, concentrated oxygen, and the like.

As shown in FIG. 1, housing 59 of portable oxygen concentrator 10 includes a plurality of walls 61 that may define outer structural surface of portable oxygen concentrator 10. Plurality of walls 61 may include a pair of side walls 63 (FIGS. 14 and 15), a front wall 65, a top wall 71, a bottom wall 69, and a rear wall 67. Portable oxygen concentrator 10 may include a carrying handle 73 connected to at least one of walls 61 (e.g., top wall 71) to enable portable oxygen concentrator 10 to be transported.

In one embodiment, housing 59 may be formed of at least two mating housing members 59A and 59B cooperating with each other to define a hollow interior 75 therein. Hollow interior 75 of housing 59 includes support member 250, sieve beds 12, reservoir 18, compressor 14 and other components of portable oxygen concentrator 10. First mating housing member 59A includes front wall 65, and at least a portion of side walls 63, bottom wall 69, top wall 71, and carrying handle 73, while second mating member 59B includes rear wall 67, and at least a portion of side walls 63, bottom wall 69, top wall 71, and carrying handle 73. First mating housing member 59A and the second mating housing member 59B may be connected to each other using any known attachment mechanism, for example, using fasteners. In another embodiment, support member 250 (with components of portable oxygen concentrator 10 attached thereon) is first connected to mating housing member 59B and the assembly of mating housing member 59B and support member 250 is then connected to mating housing member 59A.

In one embodiment, side walls 63 and/or bottom wall 69 may include one or more inlet openings 160 (FIGS. 14 and 15) that may communicate with hollow interior 75 of portable oxygen concentrator 10. Inlet openings 160 are configured to allow ambient air to pass easily through inlet openings 160, yet preventing large objects from passing therethrough.

Referring to FIGS. 1, 3-5 and 14-15, support member 250, which may form a central chassis or spine, is configured to support compressor 14, sieve beds 12, reservoir 18 and/or other components of portable oxygen concentrator 10. Support member 250 with compressor 14, sieve beds 12, reservoir 18 and/or other components of portable oxygen concentrator 10 attached thereon is disposed centrally in hollow interior 75 of housing 59.

Support member 250 may be formed from any engineering grade material, e.g., plastic, such as ABS, polycarbonate or composite materials. Support member 250 may be formed by injection molding, and the like. In another embodiment, support member 250 may be made from aluminum material or any other material suitable for machining or casting.

Referring to FIGS. 3-5 and 14-15, support member 250 with compressor 14, sieve beds 12, reservoir 18 and/or other components (e.g., controller 22, valves, etc.) of portable oxygen concentrator 10 attached thereon may first be attached to, for example, mating housing member 59A using fasteners. To attach support member 250 to mating housing member 59A, fasteners may be installed through holes 391 in attachment members 393. Then, mating housing member 59A along with support member 250 (and components of portable oxygen concentrator 10 attached thereon) may be attached to mating housing member 59B using fasteners. To attach mating housing member 59A to mating housing member 59A, fasteners may be installed through hole 417 in attachment members 419 of support member 250. Attachment members 393 with hole 391 are shown in FIG. 4A, while attachment member 419 with hole 417 are shown in FIG. 4B. In one embodiment, attachment members 393 and attachment member 419 are integrally formed or molded with support member 250.

Figure 3:
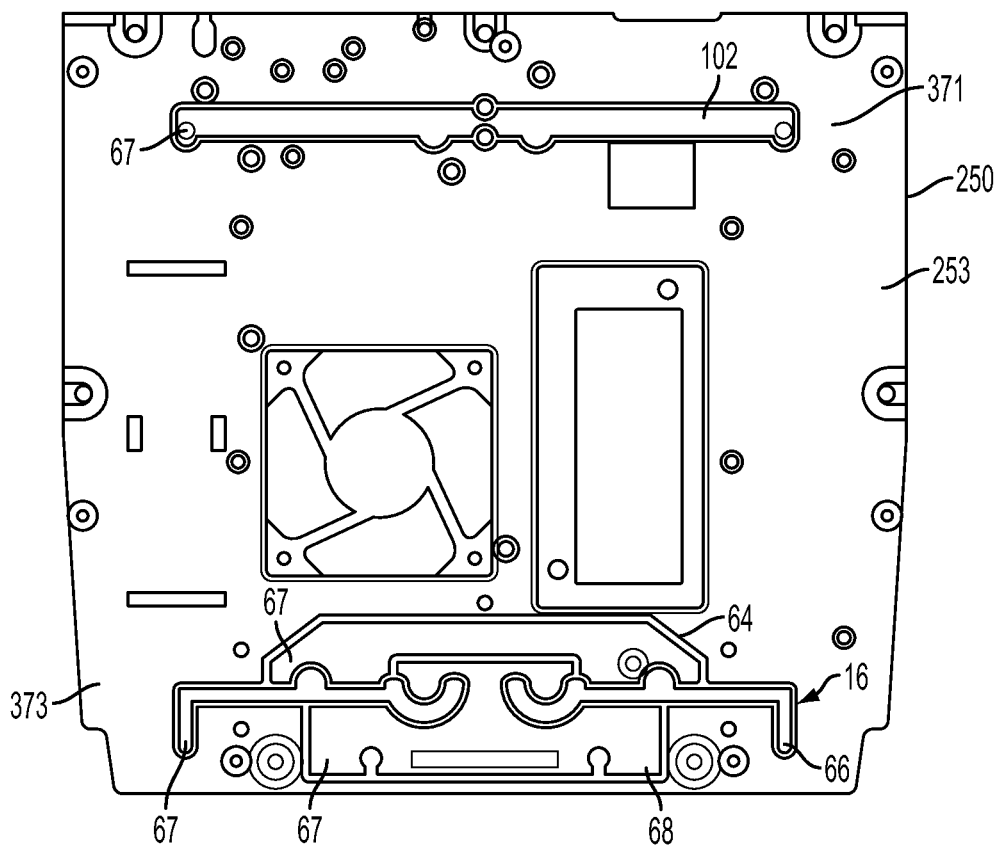
FIG. 3 is a rear view of a support member (or a central chassis) of the portable oxygen concentrator with integrally formed upper (oxygen) and lower (air) manifolds in accordance with an embodiment of the present disclosure.

Support member 250 of portable oxygen concentrator 10 has a first side surface 251 and a second side surface 253. First side surface 251 of support member 250 is shown in FIGS. 4A, and 7-13, while second side surface 253 of support member is shown in FIGS. 3 and 4B. Compressor 14 and sieve beds 12 are located on first side surface 251 of support member 250, while reservoir 18 and air control valves 20 are located on second side surface 253 of support member 250.

As shown in FIGS. 3, and 4B, air manifold 16 is integrally formed at a lower portion 371 of support member 250 and oxygen delivery manifold 102 is integrally formed at an upper portion 371 of support member 250. In one embodiment, air manifold 16 and oxygen delivery manifold 102 are integrally formed on second side surface 253 of support member 250.

As will be described below, air manifold 16 includes inlet air passages 64 and 66 for air to enter sieve beds 12 and includes exit passage 68 for nitrogen to be exhausted out of sieve beds 12 into the atmosphere. Oxygen delivery manifold 102 includes passage 108 for oxygen-enriched gas from second end ports 34 of sieve beds 12 to reservoir 18. Oxygen delivery manifold 102 also includes passage 108 and a passage 109 for oxygen-enriched gas from reservoir 18 to a device (not shown) for delivering the oxygen to a user.

Figure 4A:
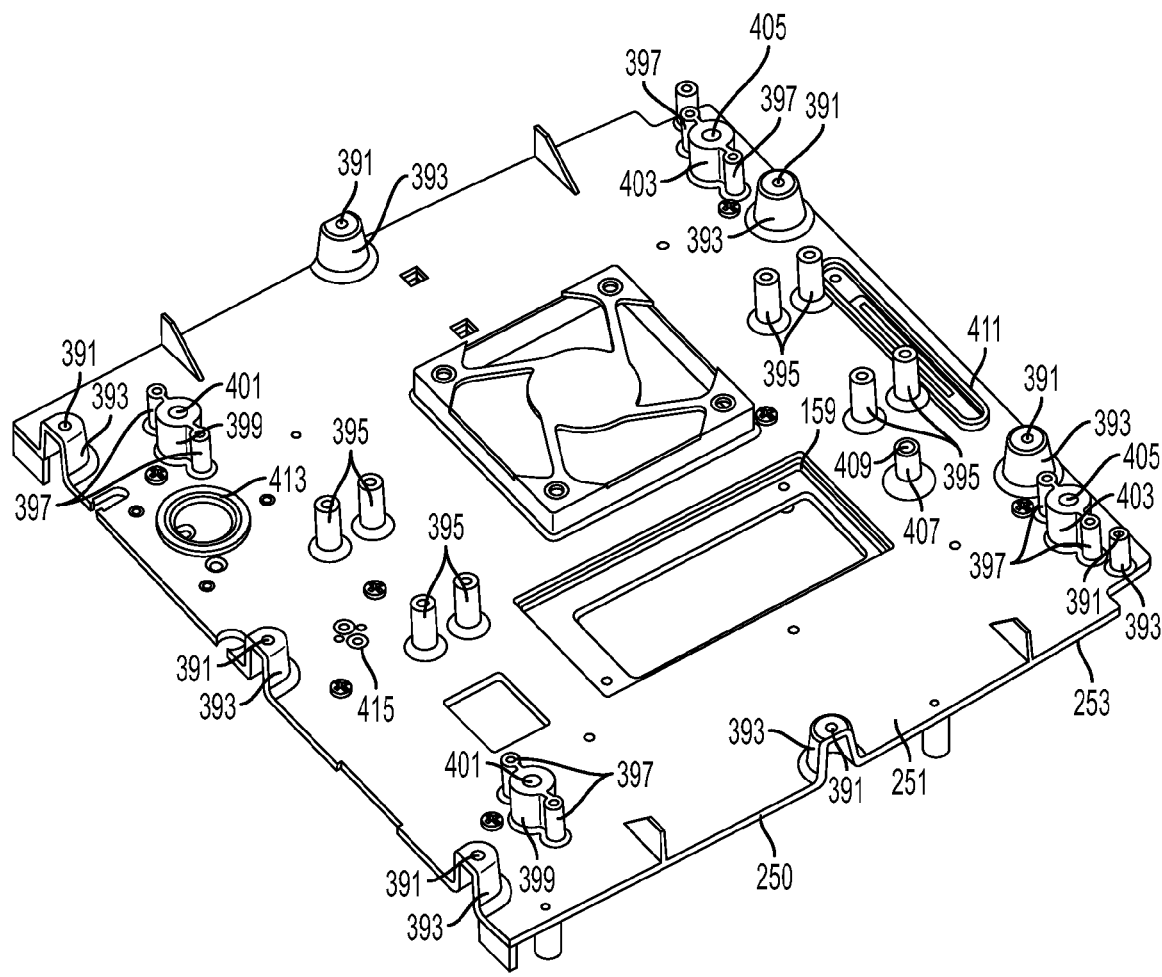
FIG. 4A is a perspective view of a first side surface of the support member in accordance with an embodiment of the present disclosure.
Figure 4B:
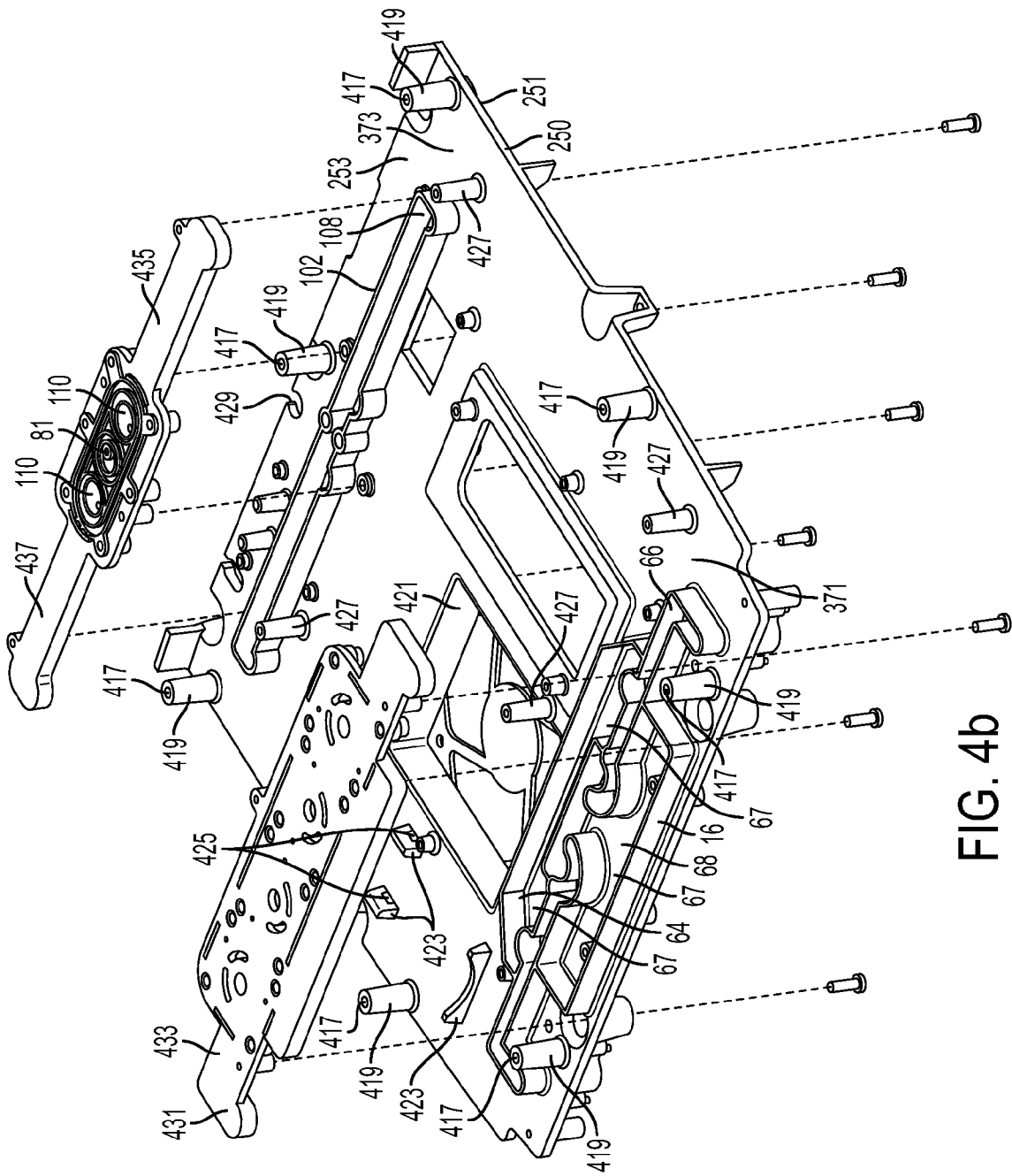
FIG. 4B is a perspective view of a second side surface of the support member with integrally formed manifolds and their respective cover members in accordance with an embodiment of the present disclosure.

FIG. 4A shows a perspective view of first side surface 251 of support member 250. A recess 159 on first side surface 251 is configured to receive an inlet air filter 162 (shown in and described with respect to FIG. 8) therein. Bracket members 165 (shown in and described with respect to FIG. 9) are used to position compressor 14 on support member 250. Bracket members 165 are attached to support member 250 using, for example, fasteners installed through holes in attachment members 395 of support member 250. In one embodiment, attachment members 395 are integrally formed or molded with support member 250.

Compressed air from compressor 14 enters a compressor outlet passage 64 of air manifold 16 through a first compressed air passage member 407. That is, first compressed air passage member 407 with an opening 409 therethrough is configured to direct or guide compressed air from a compressor outlet end 14D (and through passage members 14A-C as shown in and described with respect to FIG. 10) to compressor outlet passage 64 of air manifold 16. In one embodiment, first compressed air passage member 407 is integrally formed or molded with support member 250.

Sieve beds 12 are attached to side surface 251 of support member 250 using fasteners installed through holes in an attachment members 397 of support member 250.

Compressed air from a sieve bed inlet passage 66 of air manifold 16 enters first end ports 32 of sieve beds 12 through second compressed air passage members 403. That is, second compressed air passage members 403 with an openings 405 therethrough are configured to direct or guide compressed air from sieve bed inlet passage 66 of air manifold 16 to first end ports 32 of sieve beds 12.

Oxygen from second end ports 34 of sieve beds 12 enters oxygen delivery manifold 102 through oxygen passage members 399. That is, oxygen passage members 399 with openings 401 therethrough are configured to direct or guide oxygen from second end ports 34 of sieve beds 12 into oxygen delivery manifold 102. In one embodiment, oxygen passage members 399 and a set of second compressed air passage members 403 are integrally formed or molded with support member 250.

First side surface 251 of support member 250 also includes a muffler attachment portion 411, an air filter attachment portion 413, and an oxygen side balance valve attachment portion 415 that are configured to receive a muffler 377 (FIG. 11), an air filter 124 (FIG. 11) and an oxygen side balance valve 83 (FIG. 7) and to attach muffler 377, air filter 124 and oxygen side balance valve 83 to support member 250. The structure and operation of muffler 377, air filter 124 and oxygen side balance valve 83 will be clear from the discussions below.

Figure 2:
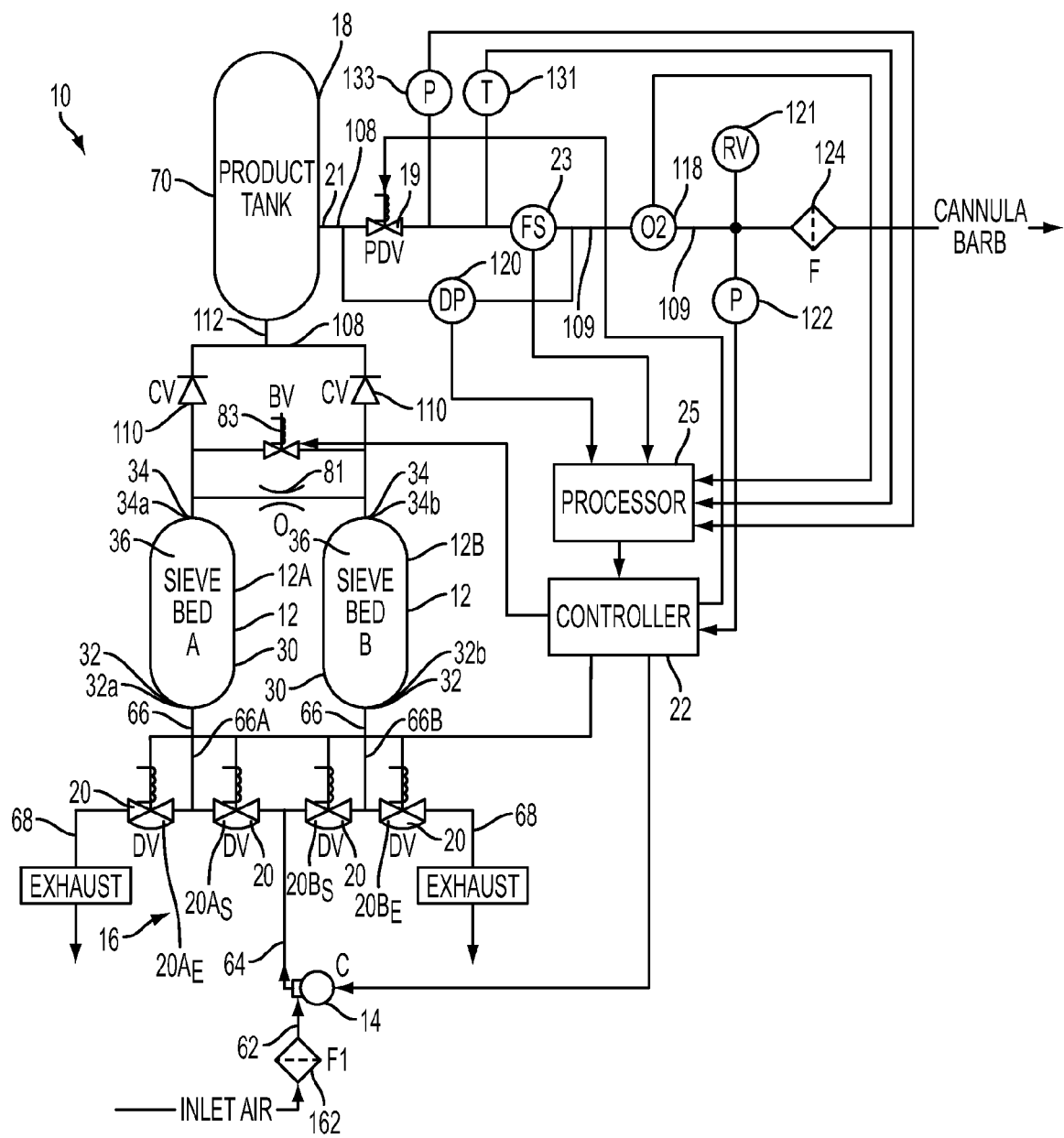
FIG. 2 schematically illustrates the portable oxygen concentrator in accordance with an embodiment of the present disclosure.

FIG. 4B shows a perspective view of second side surface 253 of support member 250. Air manifold 16 (as shown in FIGS. 2, 3 and 4B) defines a plurality of passages 66-68 therein. Air manifold 16 may include channels 67 that at least partially define compressor outlet passage 64, sieve bed inlet passage 66, and an exhaust passage 68.

Oxygen delivery manifold 102 may be provided for delivering oxygen from sieve beds 12, to reservoir 18 and then to a user of portable oxygen concentrator 10. Oxygen delivery manifold 102 may include channels 67 that at least partially define passages 108, 109 (FIG. 2) for communicating with components related to delivering oxygen to a user of portable oxygen concentrator 10. In one embodiment, channels 67 of air manifold 16 and oxygen delivery manifold 102 are integrally formed or molded with support member 250.

Air manifold 16 and oxygen delivery manifold 102 may be formed from any engineering grade material, e.g., plastic, such as ABS, polycarbonate or composite materials. Air manifold 16 and oxygen delivery manifold 102 may be formed by injection molding and the like.

Attachment members 423 on second side surface 253 of support member 250 are configured to both support and attach reservoir 18 to second side surface 253 of support member 250. In one embodiment, mounts, straps or supports (not shown) may be used to secure reservoir 18 to portable oxygen concentrator 10. For example, such mounts, straps or supports may pass through holes 425 of attachment member 423 to secure reservoir 18 to portable oxygen concentrator 10.

Attachment members 427 on second side surface 253 of support member 250 are configured to both support and attach controller 22 to second side surface 253 of support member 250. In one embodiment, attachment members 427 and 423 are integrally formed or molded with support member 250.

Second side surface 253 of support member 250 may include cutout portion that allows a tubular passage member (not shown) to pass through. For example, the tubular passage member is configured to guide or direct oxygen from air filter 124 to an overpressure relief valve 121, as will be described in detail below.

Recess 421 on second side surface 253 is configured to receive an exhaust fan (not shown) therein. The exhaust fan is configured to direct exhaust air (generally concentrated nitrogen) from exhaust passage 68 towards controller 22 or other electronics within portable oxygen concentrator 10, e.g., for cooling the electronics.

In one embodiment, attachment members 393, 395, 397, 419, 423 and 427, first compressed air passage member 407, oxygen passage members 399, and second compressed air passage members 403 are all formed of the same material as the rest of support member 250. In one embodiment, air manifold 16 and oxygen delivery manifold 102 are formed of the same material as the rest of support member 250.

Portable oxygen concentrator 10 includes an air manifold cover member 431 configured to cooperate with plurality of channels 67 of air manifold 16 to define passages 64-68 of air manifold 16. That is, air manifold cover member 431 is configured to interlock with channels 67 (of air manifold cover member 431) of support member 250 to define passages 64-68. In one embodiment, as shown in and explained with respect to FIG. 5, an upper surface 433 of air manifold cover member 431 is configured to support a set of air control valves 20 (FIG. 5) thereon.

Portable oxygen concentrator 10 includes an oxygen delivery manifold cover member 435 configured to cooperate with plurality of channels 67 of oxygen delivery manifold 102 to define passage 108. That is, oxygen delivery manifold cover member 435 is configured to interlock with channels 67 (of oxygen delivery manifold 102) of support member 250 to define passage 108. In one embodiment, as shown in and explained with respect to FIG. 6, an upper surface 437 of oxygen delivery manifold cover member 435 is configured to receive a pair of check vales 110 (FIG. 6) therein.

In one embodiment, air manifold cover member 431 and oxygen delivery manifold cover member 435 are formed of the same material as the rest of support member 250.

Figure 5:
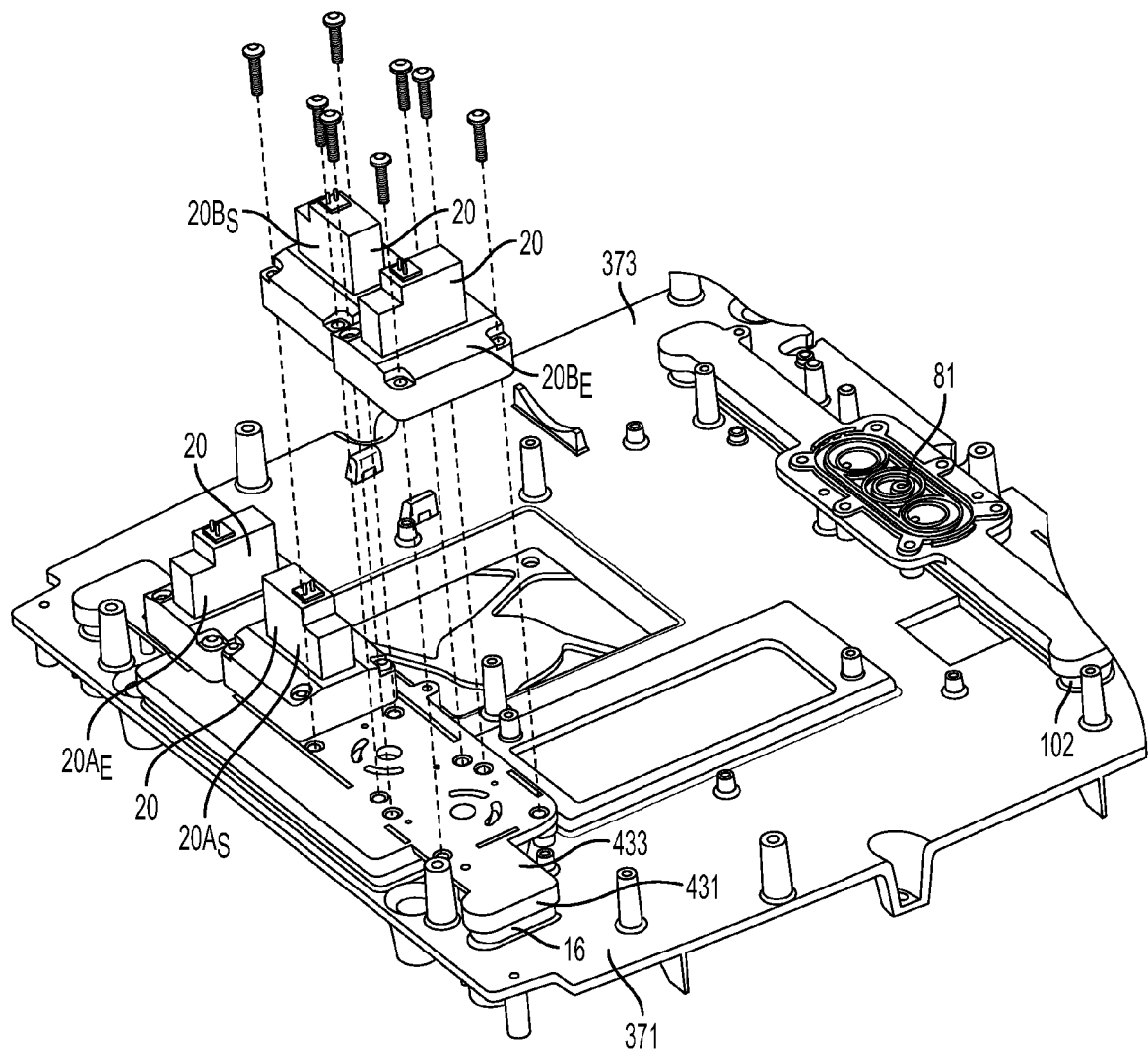
FIG. 5 is another perspective view of the second side surface of the support member with air control valves being attached thereon in accordance with an embodiment of the present disclosure.

As shown in FIGS. 2 and 5, set of air control valves 20 create one or more flow paths through passages 64-68 within air manifold 16. Air control valves 20 are in fluid communication with air manifold 16. Controller 22 may be coupled to air control valves 20 for selectively opening and closing air control valves 20 to control airflow through air manifold 16. That is, air control valves 20 may be selectively opened and closed to provide flow paths, e.g., from compressor outlet passage 64 to sieve bed inlet passage 66 and/or from sieve bed inlet passage 66 to exhaust passage 68. For example, when a supply air control valve 20AS is open, a flow path may defined from compressor 14, through compressor outlet passage 64 and an air control valve 20AS, into a sieve bed 12A. When an exhaust air control valve 20BE is open, a flow path may be defined from a sieve bed 12B, through a sieve bed inlet passage 66B and an air control valve 20BE, and into exhaust passage 68. As noted above, set of air control valves 20 attached to upper surface 433 of air manifold cover member 431 using fasteners.

Figure 6:
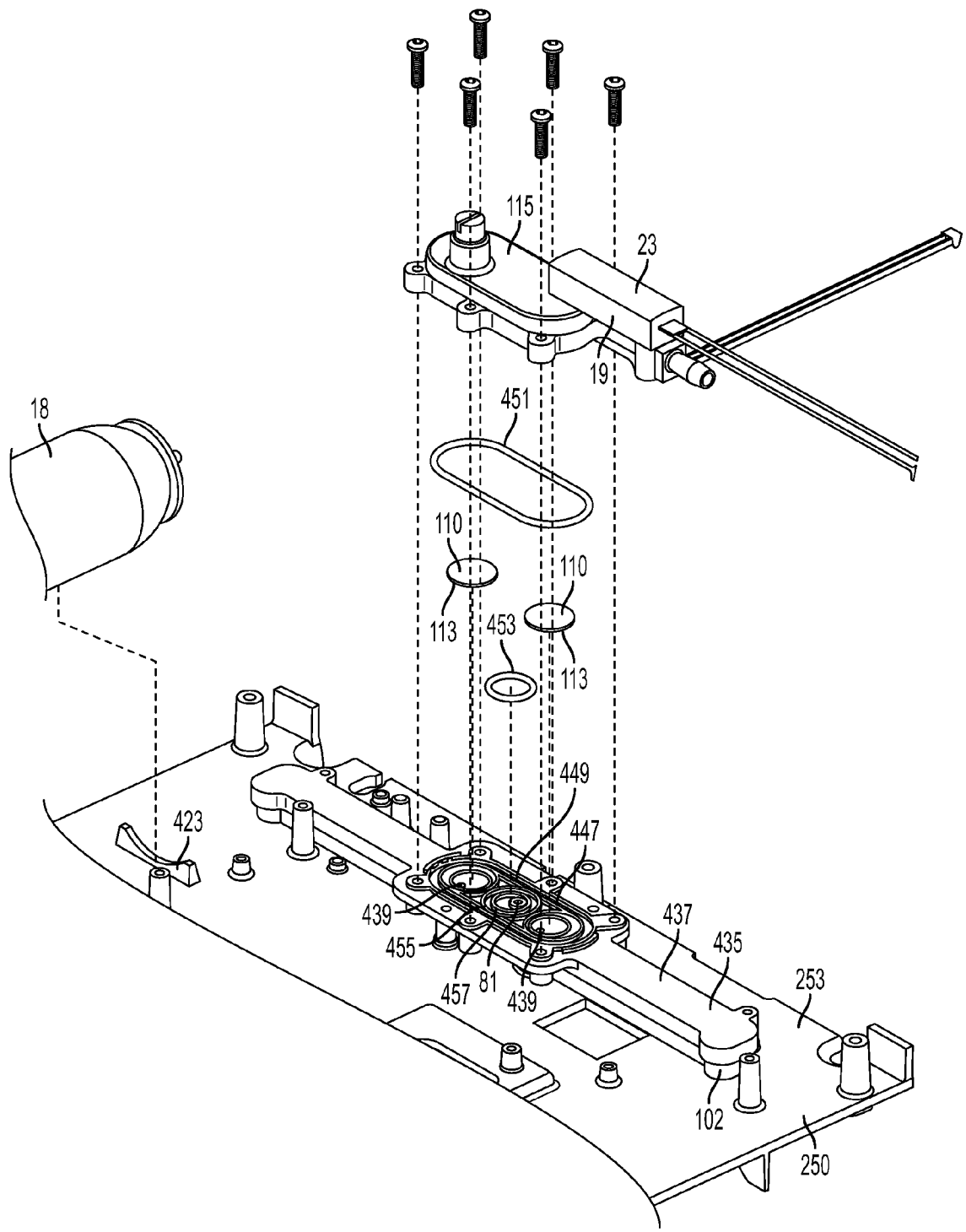
FIG. 6 is a partial perspective view of the second side surface of the support member with check valves being attached thereon in accordance with an embodiment of the present disclosure.

FIGS. 2 and 6 show check valves 110. Check valves 110 may simply be pressure-activated valves. Check valves 110 may simply be spring biased valves that open in one direction depending upon the pressure differential across the valve, such as conventional umbrella-type valves. When oxygen delivery manifold 102 is mounted to or adjacent sieve beds 12 and reservoir 18, check valves 110 provide one-way flow paths from sieve beds 12 into an oxygen delivery passage 108. Oxygen delivery passage 108 communicates directly and continuously with reservoir 18 via an opening 112 (FIG. 2).

In one embodiment, check valves 110 include check disks 113 received in received in spaces 439 formed on upper surface 437 of oxygen delivery manifold cover member 435 and a check valve cover 115 positioned in covering relation to check disks 113. Check valves 110 are attached to upper surface 437 of oxygen delivery manifold cover member 435 using fasteners. Check valves 110 are in fluid communication with oxygen delivery manifold 102. Check valves 110 may also include an O-ring 451 that is configured to sealingly engage with edges 447 of an groove 449 on upper surface 437 of oxygen delivery manifold cover member 435.

As shown in FIGS. 2 and 6, portable oxygen concentrator 10 may include a purge orifice 81 (FIGS. 5 and 6), which may provide a passage communicating directly between second end ports 34 of sieve beds 12. Optionally, an O-ring 453 may be configured to sealingly engage with edges 455 of an groove 457 on upper surface 437 of oxygen delivery manifold cover member 435. Purge orifice 81 may remain continuously open, thereby providing a passage for oxygen to pass from one sieve bed 12 to the other, e.g., while the one sieve bed 12 is charging and the other is purging. In the illustrated embodiment, as shown in FIG. 2, purge orifice 81 may be disposed upstream of check valves 110. Additional information on an exemplary purge orifice that may be included in portable oxygen concentrator 10 maybe found in U.S. Pat. No. 7,794,522, the entire disclosure of which is expressly incorporated by reference herein.

FIGS. 2 and 6 show an oxygen delivery valve 19. Oxygen delivery valve 19 may be a proportional valve that is communicating with reservoir 18 via a delivery line 21. Controller 22 receives inputs from sensors, including but not limited to a pressure sensors 120 or 122, an oxygen sensor 118 and/or a flow sensor 23. Controller is configured to control when oxygen delivery valve 19 is fully open, fully closed, or partially open as well as the degree to which oxygen delivery valve 19 is open based on the received inputs from the sensors. In one embodiment, oxygen delivery valve 19 is an adjustable restriction. For example, oxygen delivery valve 19 is a piezo-electric valve, such as a piezo-electric valve manufactured by Festo (Part or Model Number: VEMR-B-6-13-D6-W4-22X5-R5). The piezo-electric valve generally consumes low-power thereby extending the battery life of portable oxygen concentrator 10.

Flow sensor 23 is associated with a delivery line 21 and is configured to measure the instantaneous mass flow of the oxygen passing through delivery line 21 and to provide feedback to oxygen delivery valve 19. In one embodiment, flow sensor 23 is a mass flow sensor, such as a flow sensor manufactured by Honeywell (Part or Model Number: AWM 92100V) or a flow sensor manufactured by Festo (Part or Model Number 1238841).

Figure 7:
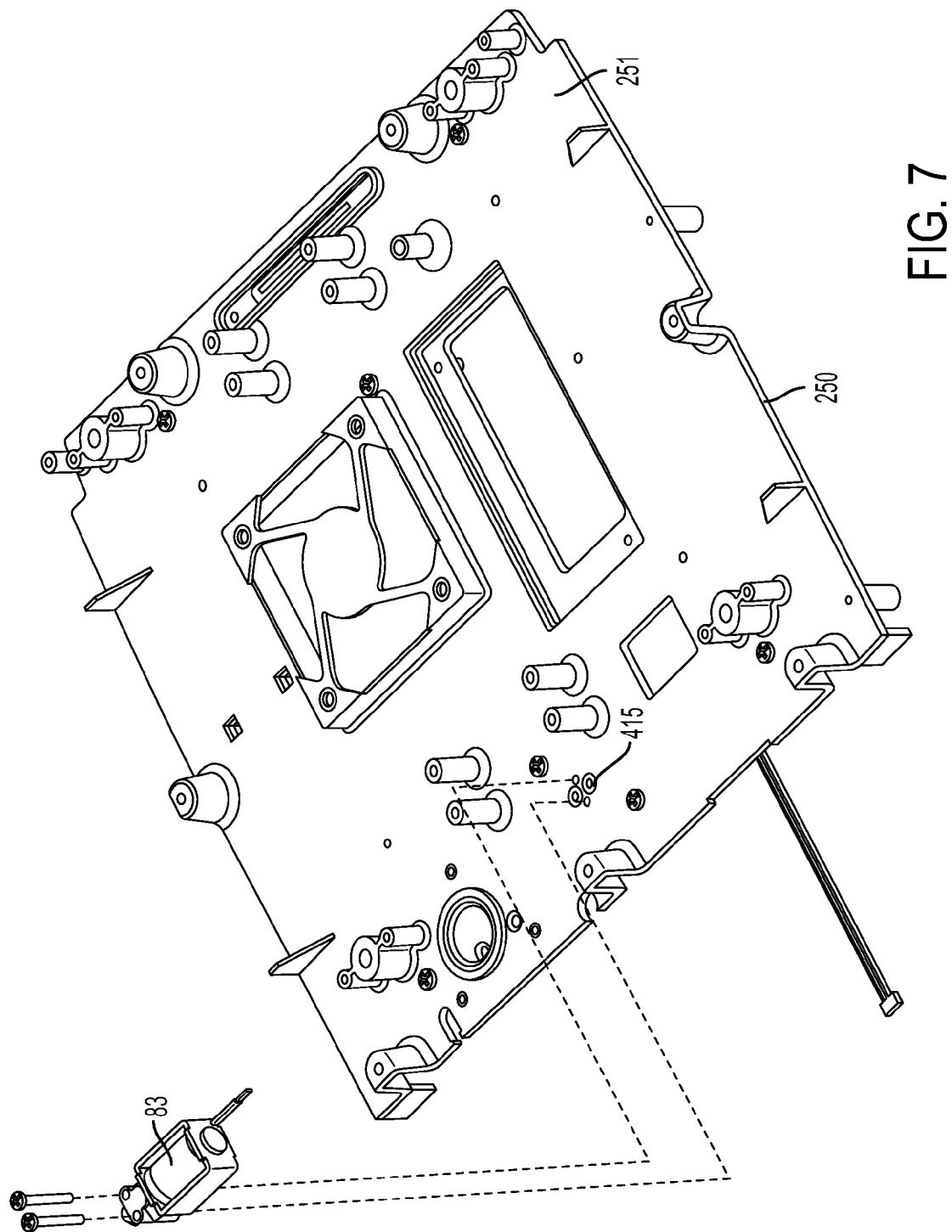
FIG. 7 shows a perspective view of the first side surface of the support member with oxygen side balance valve being attached thereon in accordance with an embodiment of the present disclosure.

FIGS. 2 and 7 show oxygen side balance valve 83. Oxygen side balance valve 83 is configured to balance bed pressures in sieve bed 12A and sieve bed 12B. During the pressure cycling of sieve beds 12, the pressure in sieve bed 12A may be higher than the pressure in sieve bed 12B indicating that the beds are not balanced. In such an instance, oxygen balance valve 83 is operated (opened) to relieve some pressure from sieve bed 12A and provide the pressure to sieve bed 12B, for example, before compressor 14 switches from sieve bed 12A to sieve bed 12B to supply compressed air to sieve bed 12B. Transferring some pressure from sieve bed 12A to sieve bed 12B allows sieve bed 12B be at some intermediate pressure (rather than be at a zero pressure), when compressor starts supplying compressed air to sieve bed 12B. Since oxygen side balance valve 83 allows sieve bed 12B be at some intermediate pressure (rather than be at a zero pressure), oxygen side balance valve 83 maximizes efficiency, e.g., to reduce power consumption of portable oxygen concentrator 10.

Oxygen side balance valve attachment portion 415 on side surface 251 of support member 250 is configured to receive and to attach oxygen side balance valve 83 to support member 250. Oxygen side balance valve 83 is in fluid communication with oxygen delivery manifold 102.

Figure 8:
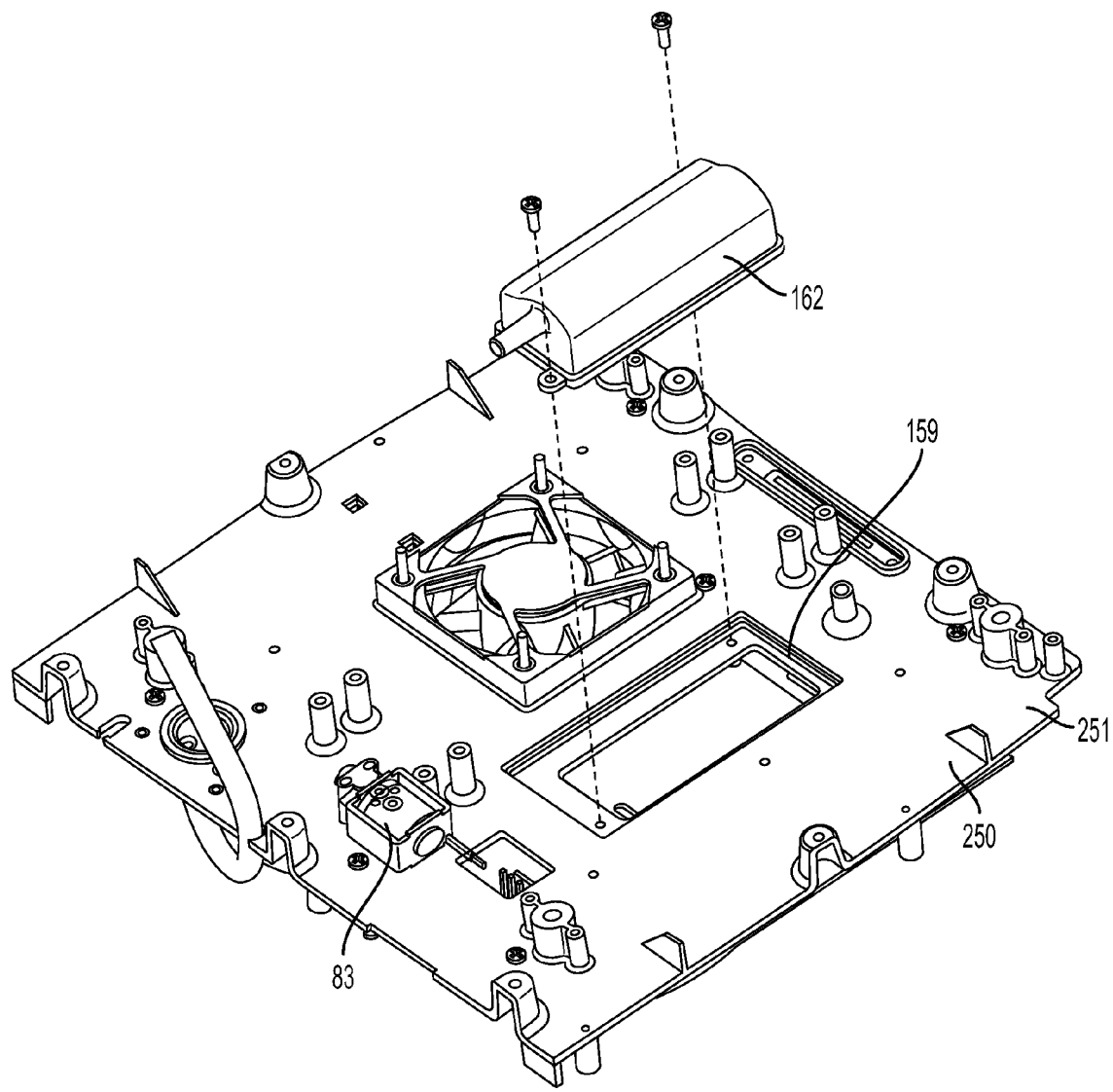
FIG. 8 shows another perspective view of the first side surface of the support member with air inlet filter being attached thereon in accordance with an embodiment of the present disclosure.

Inlet air filter 162 may be provided to remove dust or other particles from the ambient air drawn into inlet openings 160 (FIGS. 14 and 15) before it enters compressor 14. As shown in FIG. 8, inlet air filter 162 is positioned in recess 159 on first side surface 251 of support member 250 and is attached to first side surface 251 of the support member any attachment mechanism, such as fasteners.

Compressor 14 may be any device capable of drawing ambient air into portable oxygen concentrator 10 and compressing the air to one or more desired pressures for delivery to sieve beds 12. In one embodiment, compressor 14 is a multiple headed device that includes a motor, a cam assembly coupled to the motor, drive shafts or rods coupled to the cam assembly, and a plurality of diaphragm assemblies or heads coupled to the drive shafts. Additional information on an exemplary compressor that may be included in portable oxygen concentrator 10 may be found in U.S. Pat. No. 7,794,522, the entire disclosure of which is expressly incorporated by reference herein.

Figure 9:
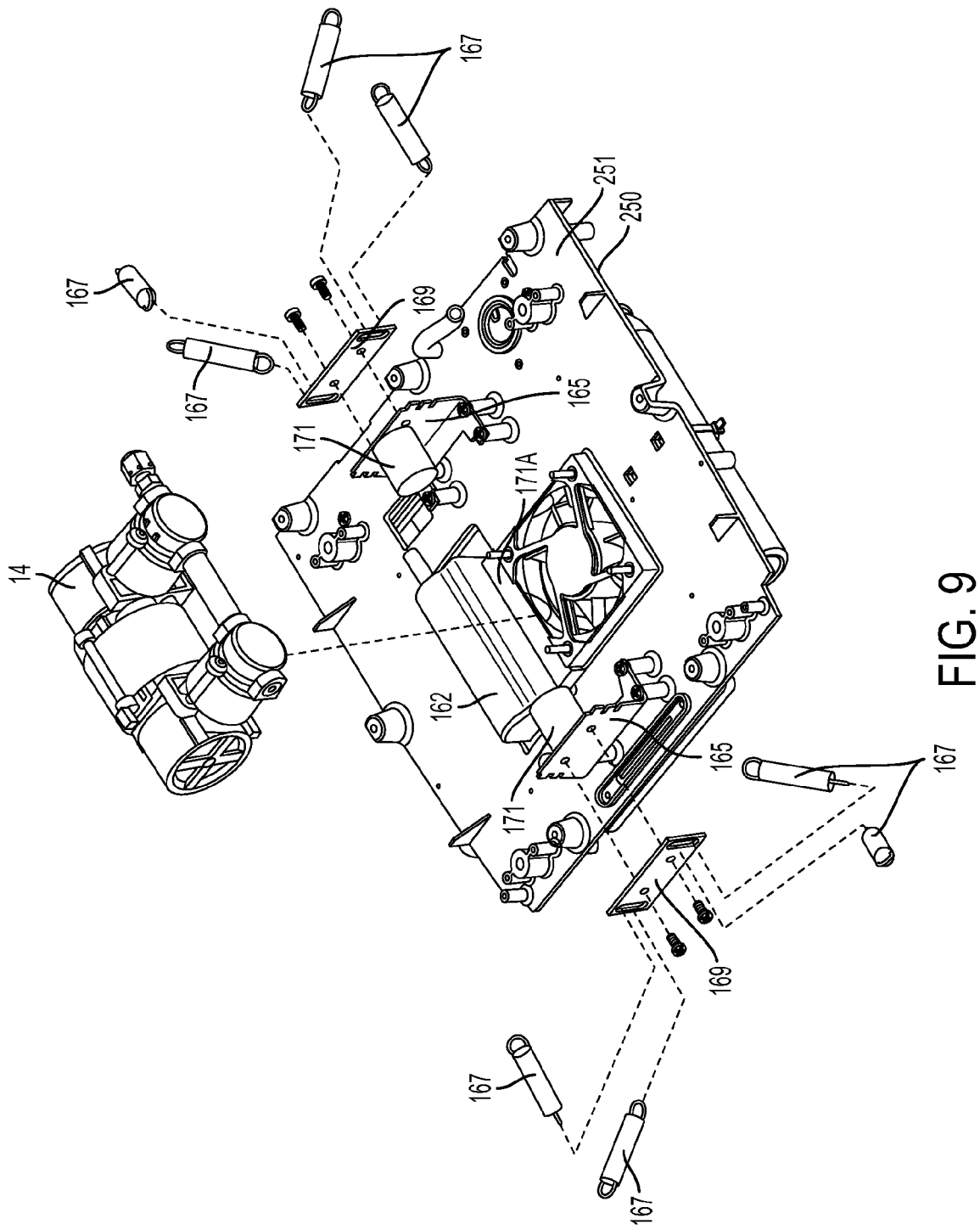
FIG. 9 shows another perspective view of the first side surface of the support member with compressor being attached thereon in accordance with an embodiment of the present disclosure.

As shown in FIG. 9, compressor 14 is positioned on first side surface 251 of support member 250 using bracket members 165. Optionally, mounting inserts (e.g., foam) 171 may be used with bracket member 165 to provide proper adequate support and damping for compressor 14. Mounting inserts 171A may also be placed between compressor 14 and side surface 251 to provide proper adequate support and noise damping for compressor 14. Compressor 14 may be secured to first side surface 251 of support member 250 using a spring lock assemblies 169 having a plurality of springs 167.

Figure 10:
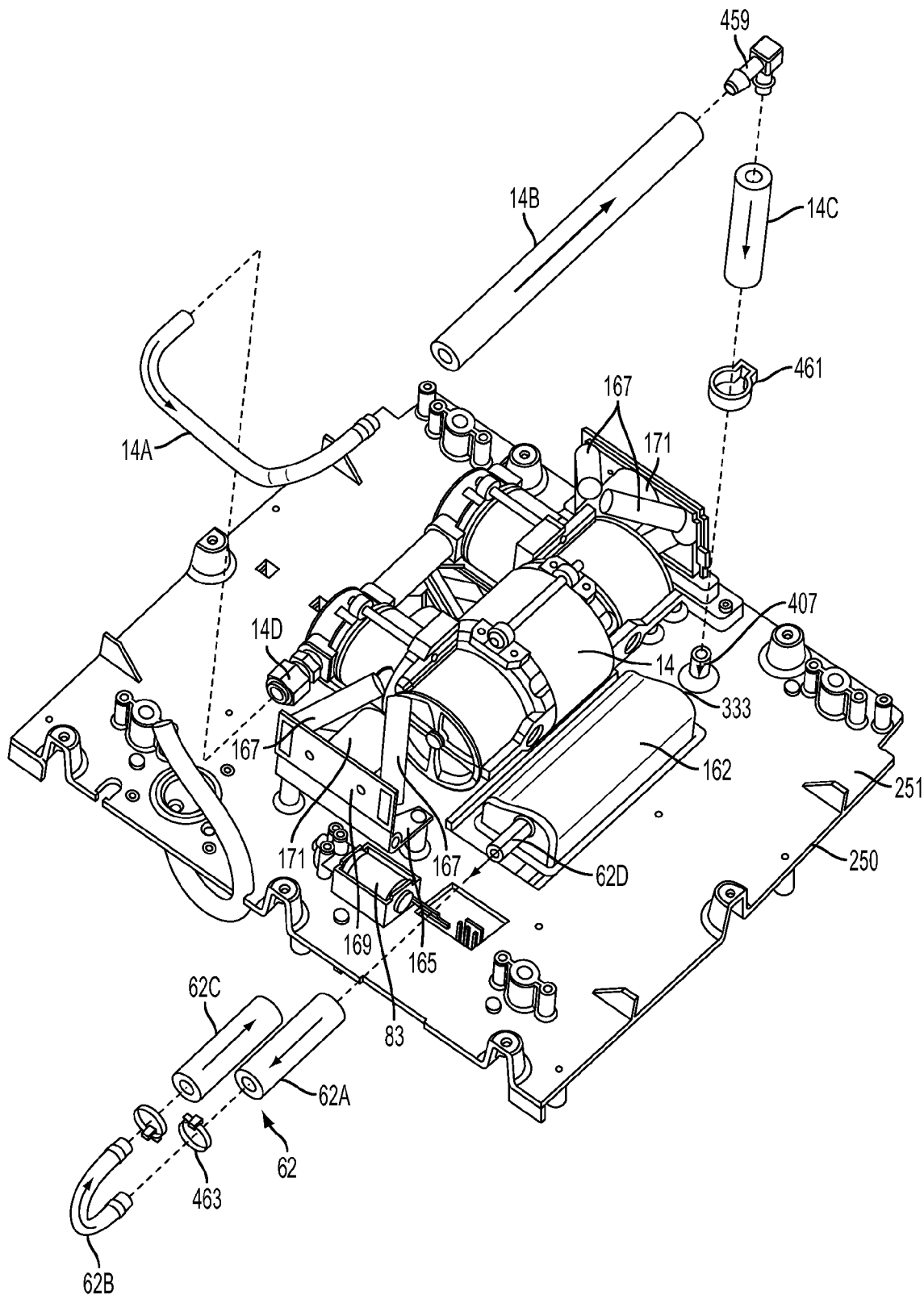
FIG. 10 shows another perspective view of the first side surface of the support member with tubing to the compressor and tubing from the compressor to air manifold being attached to the support member in accordance with an embodiment of the present disclosure.

FIG. 10 shows a compressor inlet passages 62. Passage members 62A-62C provide compressor inlet passages 62. Passage members 62A-62C are configured to direct or guide filtered air from an output end 62D of inlet filter 162 to input end (not shown) of compressor 14. Passage members 62A-62C may be connected to each other, to output end 62D of inlet filter 162 and to input end of compressor 14 such that air travels from output end 62D of inlet filter 162, successively through passage members 62A-62C and into input end of compressor 14. Passage members 62A-62C may be connected to each other, to output end 62D of inlet filter 162 and to input end of compressor 14 using cable ties 463, tee joints 459, clamps 461 and/or any other connection mechanisms. Arrows (FIG. 10) show the flow direction through passage members 62A-62C.

FIG. 10 also shows passage members 14A-C configured to direct compressed air from output end 14D of compressor 14 to compressor outlet passage 64 located in air manifold 16. Passage members 14A-C and 407 may be connected to each other and to output end 14D of compressor 14 such that compressed air travels from output end 14D of compressor 14, successively through passage members 14A-C and 407 and into compressor outlet passage 64 (disposed on second side surface 253 of support member 250) of air manifold 16. Passage members 14A-C and 407 may be connected to each other and to output end 14D of compressor 14 using cable ties, tee joints 459, clamps 461 and/or any other connection mechanisms. Arrows (FIGS. 10 and 11) show the flow direction through passage members 14A-C and 407. In one embodiment, passage member 14A and 62B have bent configurations for space efficiency.

Figure 11:
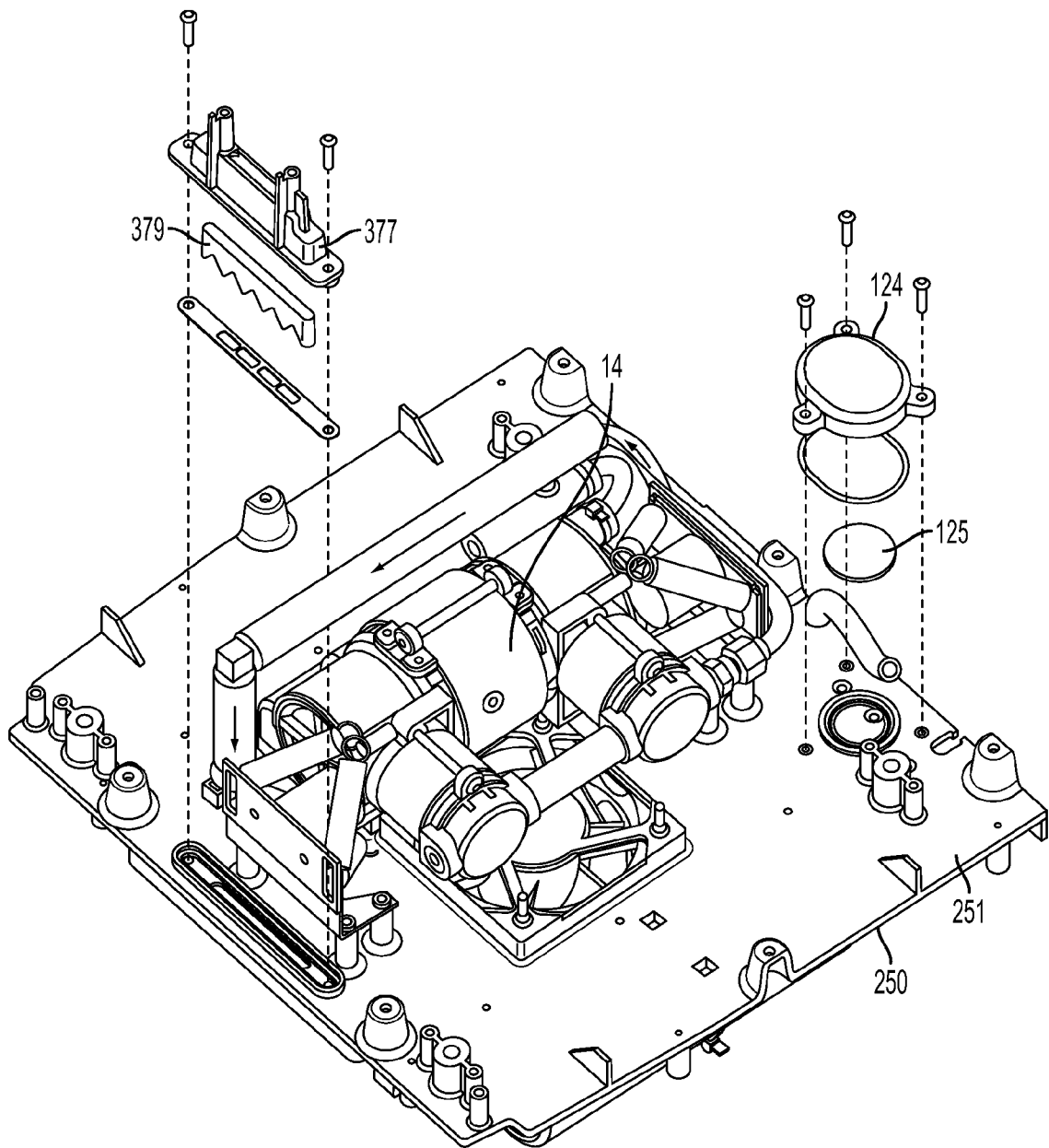
FIG. 11 shows another perspective view of the first side surface of the support member with outlet air filter and muffler being attached thereon in accordance with an embodiment of the present disclosure.

FIG. 11 shows a muffler 377 attached to first side surface 251 of support member 250. Muffler 377 with a baffle 379 may be configured for muffling the noise of compressor 14.

As shown in FIG. 11, air filter 124 may be mounted to or adjacent oxygen delivery manifold 102, and may include any a conventional filter media 125 for removing undesired particles from oxygen being delivered to the user. Air filter 124 may be attached to first side surface 251 of support member 250 using any attachment mechanism, such as fasteners. Oxygen delivered from oxygen sensor 118 (FIGS. 14 and 15) may pass through an air filter 124 and be delivered to the user.

Figure 12:
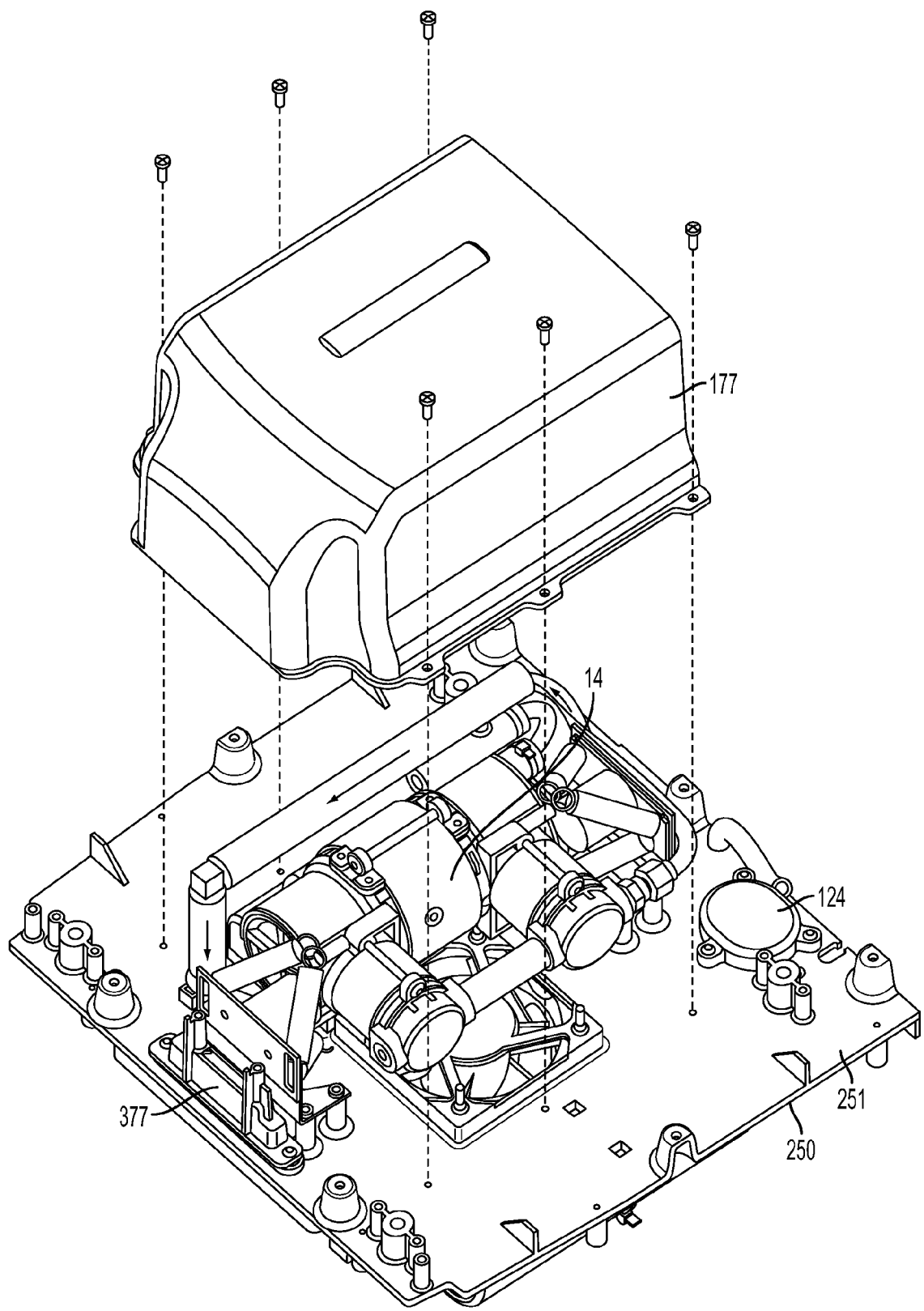
FIG. 12 shows another perspective view of the first side surface of the support member with noise shield being attached thereon in accordance with an embodiment of the present disclosure.
Figure 13:
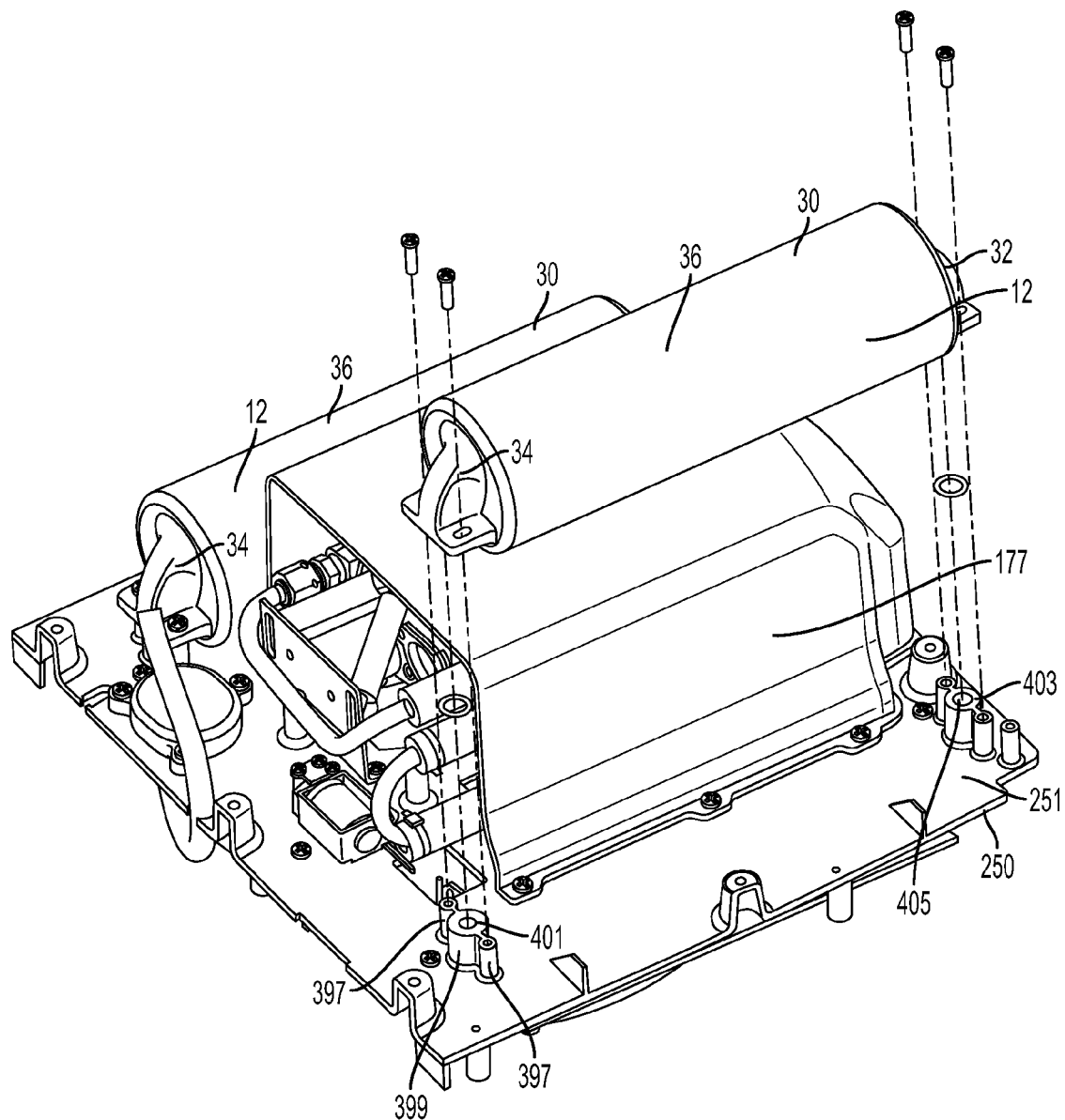
FIG. 13 shows another perspective view of the first side surface of the support member with sieve beds being attached thereon in accordance with an embodiment of the present disclosure.

Also, in order to reduce the noise level of compressor 14, a sound shield 177 (as shown in FIGS. 12 and 13) maybe formed around compressor 14 to absorb noise generated by the compressor 14. Sound shield 177 is attached to first side surface 251 using fasteners. As shown in FIG. 12, compressor 14, input air filter 162 and sound shield 177 is located on side surface 251 of support member 250. In one embodiment, sound shield 177 is made from (light weight) polypropylene material. In another embodiment, sound shield 177 is made from other plastic or composite materials.

Sieve beds 12 are configured to absorb nitrogen from air. Each sieve bed 12 includes an outer casing 30, e.g., in the shape of an elongate hollow cylinder, including first end port 32 and second end port 34. Outer casing 30 may be formed from substantially rigid material, e.g., plastic, such as acrylonitrile butadiene styrene ("ABS"), polycarbonate, and the like, metal, such as aluminum, or composite materials. Outer casing 30 may have any desired shape that may depend upon spatial, performance, and/or structural criteria. For example, outer casing 30 may have a round cylindrical shape, an elliptical, square, rectangular, or other regular or irregular polygonal shaped cross-section.

Sieve beds 12 are attached to first side surface 251 of support member 250 using fasteners installed through holes in attachment members 397 of support member 250. In one embodiment, sieve beds 12 are attached to support member 250 on both sides of sound shield 177. Each sieve bed 12 is attached to support member 250 both at its top and bottom end portions.

Oxygen from second end ports 34 of sieve beds 12 enters oxygen delivery manifold 102 through openings 401 of oxygen passage members 399. Compressed air from sieve bed inlet passage 66 of air manifold 16 enters first end ports 32 of sieve beds 12 through openings 405 of second compressed air passage members 403.

Outer casing 30 may be at least partially filled with filtration media or sieve material 36 to provide sieve bed 12 capable of adsorbing nitrogen from air delivered into sieve bed 12 under pressure. To hold sieve material 36 within casing 30, sieve bed 12 may include discs or plates (not shown) adjacent each of first end ports and second end ports 32, 34 of casing 30. The plates may be spaced apart from one another to define a desired volume between the plates and within casing 30. The plates may include one or more openings or pores (not shown) therethrough to allow airflow through the plates. Generally, sieve bed 12 may be filled such that there are no substantial voids in sieve material 36, e.g., such that sieve material 36 is substantially packed between the plates. Additional information on exemplary plates that may be included in portable oxygen concentrator 10 may be found in U.S. Pat. No. 7,794,522, the entire disclosure of which is expressly incorporated by reference herein.

Sieve material 36 may include one or more known materials capable of adsorbing nitrogen from pressurized ambient air, thereby allowing oxygen to be bled off or otherwise evacuated from sieve bed 12. Exemplary sieve materials that may be used include synthetic zeolite, LiX, and the like, such as UOP Oxysiv 5, 5A, Oxysiv MDX, or Zeochem Z10-06. It may be desirable to provide multiple layers of sieve material 36 within sieve bed 12, e.g., providing sieve material with different properties in layers between first end port 32 and second end port 34.

Although two sieve beds 12 are shown in FIG. 1, it will be appreciated that one or more sieve beds may be provided, e.g., depending upon the desired weight, performance efficiency, and the like. Additional information on exemplary sieve beds and/or sieve materials that may be included in portable oxygen concentrator 10 may be found in U.S. Pat. Nos. 4,859,217 and 7,794,522, the entire disclosures of which are expressly incorporated by reference herein.

Reservoir 18 is in communication with second end ports 34 of sieve beds 12. Reservoir 18 may include an elongate tubular casing for storing oxygen-enriched gas exiting from seconds end ports 34 of sieve beds 12. The casing of reservoir 18 may be formed from plastic, such as ABS, polycarbonate, and the like, metal, such as aluminum, or composite materials, similar to the other components of portable oxygen concentrator 10 described herein.

In a further alternative, portable oxygen concentrator 10 may include multiple reservoirs (not shown) that may be provided at one or more locations within portable oxygen concentrator 10, e.g., placed in different locations where space is available, yet minimizing the overall size of portable oxygen concentrator 10. The reservoirs may be connected to one another via one or more flexible tubes (not shown) and/or via oxygen delivery manifold 102 to allow oxygen to be delivered to and withdrawn from the reservoirs. Optionally, in this alternative, one or more valves may be provided for controlling flow of oxygen into and out of the reservoirs.

In addition or alternatively, portable oxygen concentrator 10 may include one or more flexible reservoirs, e.g., bags or other containers that may expand or contract as oxygen is delivered into or out of them. The reservoirs may have predetermined shapes as they expand or may expand elastically to fill available space within portable oxygen concentrator 10. Optionally, one or more rigid reservoirs may be provided that communicate with one or more flexible reservoirs (not shown), e.g., to conserve space within portable oxygen concentrator 10. In further alternatives, one or more reservoirs may be provided as portions of one or both of air manifold 16 and oxygen delivery manifold 102, rather than as a separate component.

Figure 14:
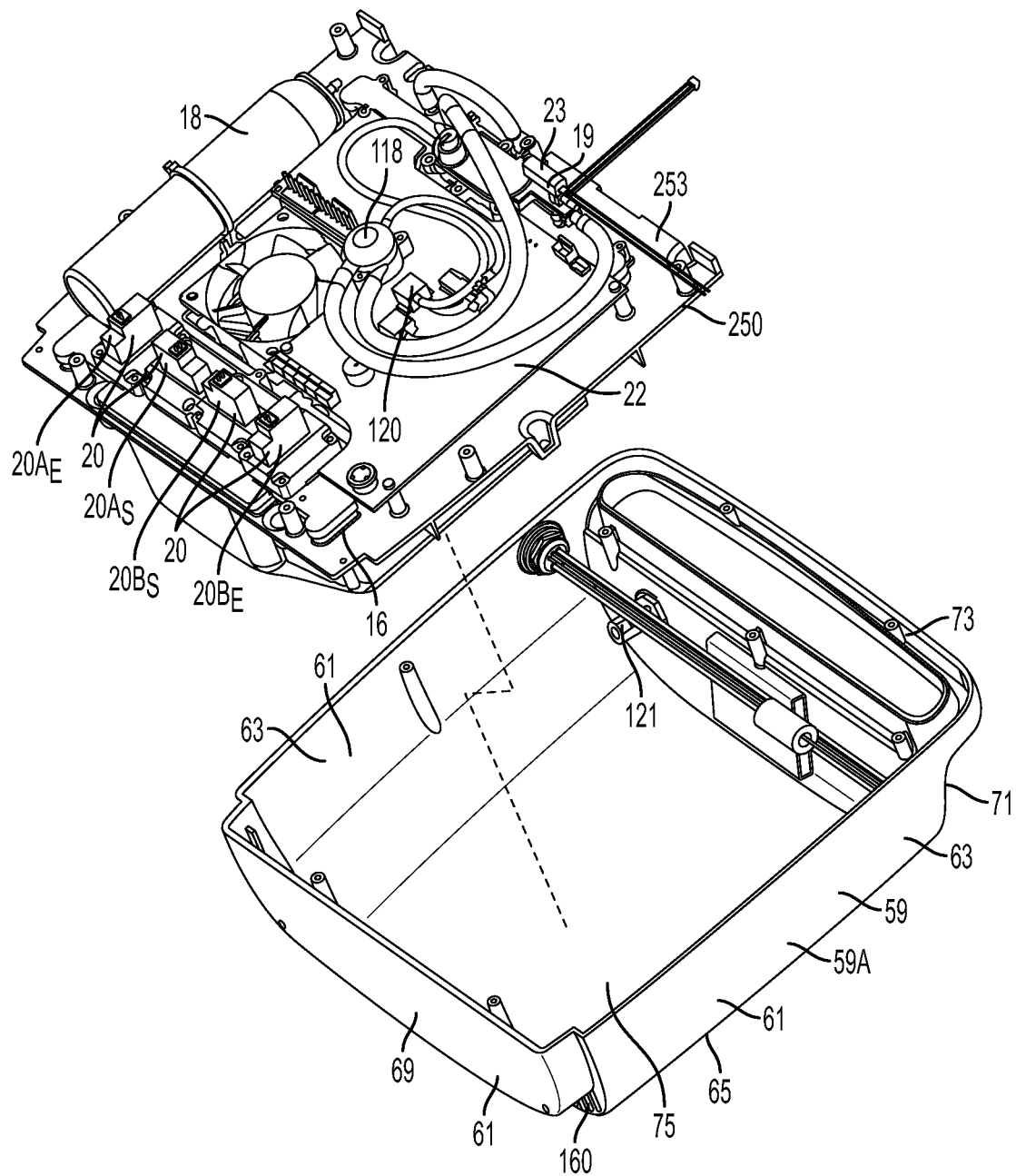
FIG. 14 is a perspective view of a housing member of the portable oxygen concentrator and the support member with reservoir, valves, and controller disposed thereon in accordance with an embodiment of the present disclosure.

As shown in FIGS. 2 and 14, oxygen sensor 118 may also be mounted to and/or below oxygen delivery manifold 102. Oxygen sensor 118 may be capable of measuring the purity of oxygen passing therethrough, e.g., an ultrasonic sensor that measures the speed of sound of the gas passing through oxygen sensor 118, such as those made by Douglas Scientific of Shawnee, Kans. Alternatively, oxygen sensor 118 may be a ceramic or sidestream sensor.

Oxygen sensor 118 may be coupled to a processor 25 and may generate electrical signals proportional to the purity that may be processed by processor 25 and used by controller 22 to change operation of portable oxygen concentrator 10. Because the accuracy of oxygen sensor 118 may be affected by airflow therethrough, it may be desirable to sample the purity signals during no flow conditions, e.g., when oxygen delivery valve 19 is closed.

As shown in FIGS. 2 and 14, portable oxygen concentrator 10 may also include an overpressure relief valve 121 pneumatically coupled into delivery line 21 to serve as a protection device for an inhalation sensor 122. Overpressure relief valve 121 allows for the use of a single supply or delivery line to be used for both pulse and continuous flow delivery from portable oxygen concentrator 10. Overpressure relief valve 121 may be set to a level below an operational proof pressure of inhalation sensor 122. If the supply circuit attempts to exceed this proof pressure, due to kinked tubing or otherwise, overpressure relief valve 121 is configured to open and maintain the pressure in the delivery circuit below a level at which inhalation sensor 122 would be damaged. An exemplary overpressure relief valve that may be included in portable oxygen concentrator 10 may be found in U.S. provisional patent application No. 61/533,912, filed Sep. 13, 2011, titled "Concentrator Supply Line Overpressure Protection," the entire disclosure of which is expressly incorporated by reference herein.

As shown in FIGS. 2 and 14, a pressure sensor 120 may also be mounted to and/or below the oxygen delivery manifold 102 such that ports of pressure sensor 120 may measure a pressure difference between passages 108, 109, and consequently across oxygen delivery valve 19. Optionally, pressure sensor 120 may be used to obtain reservoir pressure. For example, when oxygen delivery valve 19 is closed, pressure upstream of oxygen delivery valve 19 may correspond substantially to the pressure within reservoir 18.

Pressure sensor 120 may be coupled to processor 25, e.g., to provide signals that may be processed by processor 25 to determine the pressure differential across oxygen delivery valve 19. Controller 22 may use this pressure differential to determine a flow rate of the oxygen being delivered from portable oxygen concentrator 10 or other parameters of oxygen being delivered. Controller 22 may change the frequency and/or duration that oxygen delivery valve 19 is open based upon the resulting flow rates, e.g., based upon one or more feedback parameters.

As shown in FIG. 2, portable oxygen concentrator 10 includes an oxygen gas temperature sensor 131, such as a thermistor, a thermocouple, or any other temperature sensor and a local pressure sensor 133, such as a barometric pressure sensor manufactured by Freescale (Part or Model Number: MPXM2102A). Oxygen gas temperature sensor 131 is configured to measure the temperature of the oxygen passing through delivery line 21, while local pressure sensor 133 is configured to measure the local ambient pressure.

The measured oxygen temperature and the measured local ambient pressure are sent to a processor 25. Processor 25 is configured to use this oxygen temperature measurement from temperature sensor 131 and the local ambient pressure measurement from local pressure sensor 133 along with the mass flow rate measurement obtained from flow sensor 23 to obtain a volumetric flow rate measurement.

In the illustrated embodiment, as shown in FIG. 4, oxygen gas temperature sensor 131 and local pressure sensor 133 are positioned upstream of flow sensor 23. In another embodiment, oxygen gas temperature sensor 131 and local pressure sensor 133 are positioned downstream (still in the vicinity) of flow sensor 23.

Pressure sensor 122 may be coupled to oxygen delivery manifold 102. Pressure sensor 122 may be a piezo resistive pressure sensor capable of measuring absolute pressure. Pressure sensor 122 provides a pressure reading that may be used to detect when a user is beginning to inhale. Exemplary transducers that may be used include the Honeywell Microswitch 24PC01SMT Transducer, the Sensym SX01, Motorola MOX, or others made by All Sensors. Because pressure sensor 122 may be exposed to the full system pressure of portable oxygen concentrator 10, it may be desirable for the over-pressure rating of pressure sensor 122 to exceed the full system pressure. Pressure sensor 122 may be coupled to processor 25 for providing signals proportional to the pressure detected by pressure sensor 122. Additional information on an exemplary pressure sensor that may be included in portable oxygen concentrator 10 may be found in U.S. Pat. No. 7,794,522, the entire disclosure of which is expressly incorporated by reference herein.

It will be appreciated that other configurations and/or components may be provided for delivering oxygen to the user, rather than oxygen delivery manifold 102 and the components attached thereto described above. In addition, although the components, e.g., oxygen delivery valve 19, pressure sensors 120, 122, 133, flow sensor 23, oxygen sensor 118, oxygen gas temperature sensor 131 and air filter 124 are described in a particular sequence (relative to oxygen flowing through oxygen delivery manifold 102), the sequence of these components may be changed, if desired.

Controller 22 may include one or more hardware components and/or software modules that control one or more aspects of the operation of portable oxygen concentrator 10. Controller 22 may be coupled to one or more components of portable oxygen concentrator 10, e.g., compressor 14, air control valves 20, and/or oxygen delivery valve 19. Controller 22 may also be coupled to one or more sensing components of portable oxygen concentrator 10, e.g., pressure sensors 120, 122, oxygen gas temperature sensor 131, local pressure sensor 133, flow sensor 23 and/or oxygen sensor 118 via processor 25. The components may be coupled by one or more wires or other electrical leads capable of receiving and/or transmitting signals between controller 22 and the components.

Controller 22 may also be coupled to a user interface 320, which may include one or more displays and/or input devices. User interface 320 may be a touch-screen display that may be mounted to portable oxygen concentrator 10. User interface 320 may display information regarding parameters related to the operation of portable oxygen concentrator 10 and/or allow the user to change the parameters, e.g., turn portable oxygen concentrator 10 on and off, change dose setting or desired flow rate, etc. Portable oxygen concentrator 10 may include multiple displays and/or input devices, e.g., on/off switches, dials, buttons, and the like. User interface 320 may be coupled to controller 22 by one or more wires and/or other electrical leads (not shown for simplicity), similar to the other components.

Controller 22 may include a single electrical circuit board that includes a plurality of electrical components thereon. These components may include one or more processors, memory, switches, fans, battery chargers, and the like (not shown) mounted to the circuit board. It will be appreciated that controller 22 may be provided as multiple subcontrollers that control different aspects of the operation of portable oxygen concentrator 10. For example, a first subcontroller may control operation of compressor 14 and the sequence of opening and closing of air control valves 20, e.g., to charge and purge sieve beds 12 in a desired manner. Additional information on an exemplary first subcontroller that may be included in portable oxygen concentrator 10 may be found in U.S. Pat. No. 7,794,522, the entire disclosure of which is expressly incorporated by reference herein.

A second subcontroller may control operation of oxygen delivery valve 19, e.g., to deliver oxygen from reservoir 18 to a user based upon signals received from pressure sensor 120, from flow sensor 23, from oxygen gas temperature sensor 131 and from local pressure sensor 133. The second subcontroller may also receive input instructions from the user and/or display information on user interface 320. In addition, the subcontrollers or other components of controller 22 may share information in a desired manner, as described below. Thus, controller 22 may include one or more components, whose functionality may be interchanged with other components, and controller 22 should not be limited to the specific examples described herein.

Portable oxygen concentrator 10 may include one or more power sources, coupled to controller 22, processor 25, compressor 14, air control valves 20, and/or an oxygen delivery valve 23. For example, a pair of batteries may be provided that may be mounted or otherwise secured to portable oxygen concentrator 10. In one embodiment, batteries may be provided in a battery compartment 361 (FIG. 1). Mounts, straps or supports (not shown) may be used to secure the batteries to portable oxygen concentrator 10. Additional information on exemplary batteries that may be included in portable oxygen concentrator 10 may be found in U.S. Pat. No. 7,794,522, the entire disclosure of which is expressly incorporated by reference herein.

Controller 22 may control distribution of power from batteries 148 to other components within portable oxygen concentrator 10. For example, controller 22 may draw power from one of batteries 148 until its power is reduced to a predetermined level, whereupon controller 22 may automatically switch to the other of batteries 148.

Optionally, portable oxygen concentrator 10 may include an adapter such that an external power source, e.g., a conventional AC power source, such as a wall outlet, or a portable AC or DC power source, such as an automotive lighter outlet, a solar panel device, and the like (not shown). Any transformers or other components (also not shown) necessary to convert such external electrical energy such that it may be used by portable oxygen concentrator 10 may be provided within portable oxygen concentrator 10, in the cables connecting portable oxygen concentrator 10 to the external power source, or in the external device itself.

Optionally, controller 22 may direct some electrical energy from external sources back to batteries 148 to recharge them in a conventional manner. Controller 22 may also display the status of the electrical energy of portable oxygen concentrator 10, e.g., automatically or upon being prompted via user interface 320, such as the power level of batteries 148, whether portable oxygen concentrator 10 is connected to an external power source, and the like. Controller 22 may include one or more dedicated components for performing one or more of these functions. An exemplary battery management integrated circuit that may be included in controller 22 of portable oxygen concentrator 10 may be found in U.S. Pat. No. 7,794, 522, the entire disclosure of which is expressly incorporated by reference herein.

Processor 25 of portable oxygen concentrator 10 may be configured to receive the signals from one or more sensing components of portable oxygen concentrator 10, e.g., flow sensor 23, oxyten gas temperature sensor 131, local pressure sensor 133 and/or pressure sensor 120 to determine a flow of the oxygen-enriched gas in the delivery line over a predetermined period of time, a volume of the oxygen-enriched gas in the delivery line over a predetermined period of time or both based on the received signal.

Portable oxygen concentrator 10 may also include a dynamic noise control that is configured to dynamically change an inlet port size or shape of the inlet air filter 162 proportionately for all input/output settings. For example, the higher the volume of air needed the larger the input port size and vice versa. An exemplary dynamic noise control that may be included in portable oxygen concentrator 10 may be found in co-pending U.S. provisional patent application No. 61/533,864, filed Sep. 13, 2011, entitled "Oxygen Concentrator With Dynamic Noise Control," the entire disclosure of which is expressly incorporated by reference herein.

The basic operation of portable oxygen concentrator 10 will now be described. Generally, operation of portable oxygen concentrator 10 has two aspects, concentrating oxygen from ambient air by adsorption within sieve beds 12, and delivering concentrated oxygen to a user from reservoir 18. Each aspect of portable oxygen concentrator 10 may operate independently of the other, or they may be interrelated, e.g., based upon one or more related parameters.

Portable oxygen concentrator 10 may be operated using one or more optional methods, such as those described below, to increase efficiency or other performance characteristics of portable oxygen concentrator 10. For example, based upon measurements of pressure and/or flow sensors, the operating conditions of portable oxygen concentrator 10 may be adjusted to increase output flow rate and/or pressure, reduce power consumption, and the like.

Figure 15:
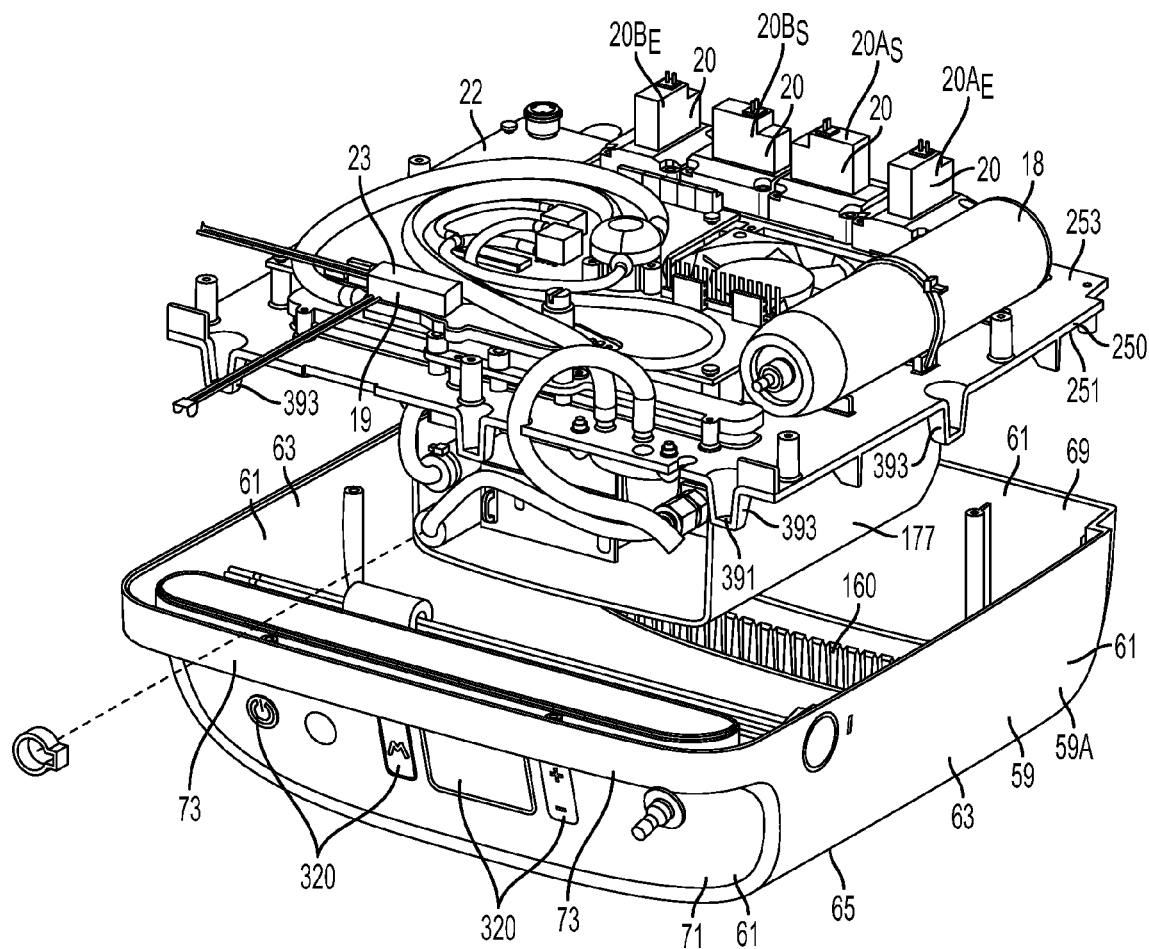
FIG. 15 is another perspective view of the housing member and the support member of the portable oxygen concentrator in accordance with an embodiment of the present disclosure.

The aspects of receiving ambient air, filtering the ambient air, compressing the ambient air, delivering the compressed air to air manifold 16 are described by referring FIGS. 2, 10 and 15.

As shown in FIG. 15, ambient air enters hollow interior 75 of housing 59 through one or more inlet openings 160 (FIGS. 14 and 15) located on bottom wall 69. As noted above, inlet openings 160 are configured to allow the ambient air to pass easily through inlet openings 160, yet preventing large objects from passing therethrough.

Referring to FIGS. 2 and 10, the ambient air in hollow interior 75 enters inlet air filter 162 through an opening (e.g., located on side 333) of inlet air filter 162. Inlet air filter 62 may be provided before the inlet port of compressor 14 to remove dust or other particles from the ambient air drawn into inlet opening 160 before it enters compressor 14.

Filtered air travels from output end 62D of inlet filter 162, successively through passage members 62A-62C, and into the input end of compressor 14. Arrows (FIG. 10) show the flow direction of filtered air through passage members 62A-62C.

Filtered air entering compressor 14 is compressed therein. Compressed air travels from output end 14D of compressor 14, successively through passage members 14A-C and 407 and into compressor outlet passage 64 of air manifold 16. Arrows (FIGS. 10 and 11) show the flow direction through passage members 14A-C and 407. Compressed air enters compressor outlet passage 64 of air manifold 16 through compressed air passage member 407.

Referring to FIGS. 2, 4A, 4B and 5, air control valves 20 are configured to create one or more flow paths through passages 64-68 within air manifold 16. As noted above, air control valves 20 may be selectively opened and closed to provide flow paths, e.g., from compressor outlet passage 64 to sieve bed inlet passage 66 and/or from the sieve bed inlet passage 66 to the exhaust passage 68.

The compressed air in sieve bed inlet passage 66 are guided or directed to first end ports 32 of sieve beds 12 via second compressed air passage members 403. The aspect of concentrating oxygen from ambient air by adsorption within sieve beds 12 is explained in great detail in U.S. Pat. No. 7,794,522, the entire disclosure of which is expressly incorporated by reference herein. Exhaust passage 68 communicates with sieve beds 12 to evacuate nitrogen from sieve beds 12.

Concentrated oxygen from second port ends 34 of sieve beds 12 enters oxygen delivery manifold 102 via oxygen passage members 399. Check valves 110 in oxygen delivery manifold 102 provide one-way flow paths from second port ends 34 of sieve beds 12 into oxygen delivery passage 108. Concentrated oxygen is delivered to reservoir 18 via passages 108 of oxygen delivery manifold 102.

With concentrated oxygen stored in reservoir 18, portable oxygen concentrator 10 may be used to deliver concentrated oxygen to a user. As described above, controller 22 may be coupled to oxygen delivery valve 19 for opening and closing oxygen delivery valve 19 to deliver oxygen from reservoir 18 to a user of portable oxygen concentrator 10.

In one embodiment, controller 22 may periodically open oxygen delivery valve 19 for predetermined "pulses." During pulse delivery, a "bolus" of oxygen is delivered to the user, i.e., oxygen delivery valve 19 is opened for a predetermined pulse duration, and thereafter closed until the next bolus is to be delivered. Alternatively, controller 22 may open oxygen delivery valve 19 for continuous delivery, e.g., throttling oxygen delivery valve 19 to adjust the flow rate to the user. In a further alternative, controller 22 may periodically open and throttle oxygen delivery valve 19 for a predetermined time to vary the volume of the bolus delivered.

The aspect of controlling opening and closing oxygen delivery valve 19 to deliver the oxygen-enriched gas from reservoir 18 to a user using flow sensor 23 and/or pressure sensor 120 is explained in detail in co-pending U.S. provisional patent application No. 61/533,871, filed Sep. 13, 2011, titled "Proportional Oxygen Conserving Device With Flow Sensing," the entire disclosure of which is expressly incorporated by reference herein.

The present disclosure also provides a method of manufacturing a portable oxygen concentrator. The method includes forming support member 250 configured to support compressor 14, sieve beds 12 and reservoir 18, integrally forming air manifold 16 at a lower portion of support member 250, and integrally forming oxygen delivery manifold 102 at upper portion 371 of support member 250. The method further includes integrally forming first compressed air passage member 407, second compressed air passage members 403 and oxygen passage members 399 with support member 250 and integrally forming attachment members 393, 395, 397, 419 and 427 with support member 250.

The method also includes attaching compressor 14 and sieve beds 12 to first side surface 251 of support member 250, attaching reservoir 18 to second side surface 253 of support member 250, attaching air manifold cover member 431 to air manifold 16 on support member 250, and attaching oxygen delivery manifold cover member 435 to oxygen delivery manifold 102 on support member 250. Attaching other components of portable oxygen concentrator 10, including but not limited to valves, controller, processor, sensors, sound shield, muffler, tubing or passage members, and filters to support member 250.

Support member 250 with components of portable oxygen concentrator 10 attached thereon is connected to one of mating housing members 59A and 59B. The mating housing member and support member 250 assembly is then connected to other of mating housing members 59A and 59B.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the embodiments have been described in detail for the purpose of illustration based on what is currently considered to be most practical and preferred, it is to be understood that such detail is solely for that purpose and does not impose any limits, but, on the contrary, the disclosure is intended to cover modifications and equivalent arrangements that are within the spirit and scope of the appended claims. For example, it is to be understood that, to the extent possible, one or more features of any embodiment are contemplated to be combined with one or more features of any other embodiment.

What is claimed is:

1. A portable oxygen concentrator, comprising:
a housing;
a plurality of sieve beds configured to absorb nitrogen from air, wherein the plurality of sieve beds includes a first sieve bed and a second sieve bed, wherein the first sieve bed includes a first upstream port and a first downstream port, wherein the second sieve bed includes a second upstream port and a second downstream port;
a reservoir configured to store oxygen-enriched gas exiting from the first downstream port and the second downstream port;
a compressor configured to deliver air at one or more desired pressures to the first upstream port and the second upstream port, wherein the compressor includes a compressor outlet;
a support member positioned in the housing and configured to support the compressor, the plurality of sieve beds and the reservoir, wherein the plurality of sieve beds and the reservoir are on opposite sides of the support member;
an air manifold providing a first plurality of channels therein define at least a portion of a plurality of passages communicating between the compressor outlet and the plurality of sieve beds, wherein the plurality of passages includes a first passage between the compressor outlet and the second upstream port of the second sieve bed; and
an oxygen delivery manifold providing a second plurality of channels therein that define at least a portion of one or more passages for delivery of the oxygen-enriched gas to a user, wherein the support member, air manifold, and the oxygen delivery manifold are integrally injection molded and constructed from the same material.

2. The portable oxygen concentrator of claim 1, wherein the air manifold is integrally formed at a lower portion of the support member and the oxygen delivery manifold is integrally formed at an upper portion of the support member.

3. The portable oxygen concentrator of claim 1, wherein the one or more passages defined in the oxygen delivery manifold for delivery of the oxygen-enriched gas from the plurality of sieve beds to the user include a first reservoir passage between the first downstream port and the reservoir, and a second reservoir passage between the second downstream port and the reservoir, and an oxygen delivery passage between the reservoir and a device for delivery of oxygen-enriched gas to the user.

4. The portable oxygen concentrator of claim 1, wherein the plurality of passages defined in the air manifold further includes an exhaust passage to exhaust nitrogen into atmosphere from the first upstream port and from the second upstream port.

5. The portable oxygen concentrator of claim 1, further comprising an air manifold cover member configured to cooperate with the support member to define the plurality of passages of the air manifold.

6. The portable oxygen concentrator of claim 1, further comprising an oxygen delivery manifold cover member configured to cooperate with the support member to define at least a portion of the one or more passages for delivery of oxygen-enriched gas to the user.

7. A system configured to concentrate oxygen, the system comprising:
compressing means for generating a supply of compressed air from a supply of air;
separating means for providing a supply of oxygen-enriched gas from the supply of compressed air;
oxygen storing means for storing the oxygen-enriched gas;
supporting means for supporting the compressing means, the separating means and the oxygen storing means wherein the separating means and the oxygen storing means are on opposite sides of the supporting means;
air delivery means for communicating air through a first plurality of channels that define at least a portion of a plurality of passages communicating between the compressing means and the separating means; and
oxygen delivery means for communicating the oxygen-enriched gas through a second plurality of channels that define at least a portion of one or more passages for delivery of the oxygen-enriched gas to a user, wherein the supporting means, air delivery means, and the oxygen delivery means are integrally injection molded and constructed from the same material.

8. The system of claim 7, wherein the air delivery means is integrally formed at a lower portion of the supporting means and the oxygen delivery means is integrally formed at an upper portion of the supporting means.

9. The system of claim 7, wherein the plurality of passages defined in the air delivery means include one or more passages between the separating means and atmosphere to exhaust nitrogen, and wherein the one or more passages defined in the oxygen delivery means for delivery of the oxygen-enriched gas from the separating device to the user include a first passage between the separating means and the oxygen storing means and a second passage between the oxygen storage means and a device for delivery of oxygen-enriched gas to the user.

10. A method of manufacturing a portable oxygen concentrator, the portable oxygen concentrator comprising a housing; a plurality of sieve beds, wherein the plurality of sieve beds includes a first sieve bed and a second sieve bed, wherein the first sieve bed includes a first upstream port and a first downstream port, wherein the second sieve bed includes a second upstream port and a second downstream port, a reservoir storing oxygen-enriched gas exiting from the first downstream port and the second downstream port, and a compressor, the method comprising:
forming a support member configured to support the compressor, the plurality of sieve beds and the reservoir, the support member configured to be positioned in the housing wherein the plurality of sieve beds and the reservoir are on opposite sides of the support member;

integrally injection molding an air manifold with the support member, the air manifold comprising a first plurality of channels therein that define at least a portion of a plurality of passages communicating between the compressor and the plurality of sieve beds; and integrally injection molding an oxygen delivery manifold with the support member, the oxygen delivery manifold comprising a second plurality of channels therein that define at least a portion of one or more passages for delivery of the oxygen-enriched gas to a user, wherein the support member, air manifold, and oxygen delivery manifold are constructed from the same material.

11. The method of claim 10, wherein the air manifold is integrally formed at a lower portion of the support member and the oxygen delivery manifold is integrally formed at an upper portion of the support member.

12. The method of claim 10, further comprising attaching the compressor and the plurality of sieve beds to a first side surface of the support member and attaching the reservoir to a second side surface of the support member.

13. The method of claim 10, wherein the plurality of passages defined in the air manifold includes an exhaust passage to exhaust nitrogen into atmosphere from the sieve beds.

14. The method of claim 10, further comprising attaching an air manifold cover member to the air manifold on the support member, wherein the air manifold cover member cooperates with the support member to define the plurality of passages of the air manifold.

15. The method of claim 10, further comprising attaching an oxygen delivery manifold cover member to the oxygen delivery manifold on the support member, wherein the oxygen delivery manifold cover member cooperates with the support member to define the one or more passages of the oxygen delivery manifold.

16. The method of claim 10, wherein the one or more passages defined in the oxygen delivery manifold include a first passage between the plurality of sieve beds and the reservoir and a second passage between the reservoir and a device for delivery of oxygen-enriched gas to the user.

* * * * *